US010962551B2

United States Patent
Wong et al.

(10) Patent No.: US 10,962,551 B2
(45) Date of Patent: Mar. 30, 2021

(54) TDP-43 IN DEGENERATIVE DISEASE

(71) Applicant: THE JOHNS HOPKINS UNIVERSITY, Baltimore, MD (US)

(72) Inventors: Philip C. Wong, Lutherville, MD (US); Jonathan P. Ling, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/737,489

(22) PCT Filed: Jun. 17, 2016

(86) PCT No.: PCT/US2016/038037

§ 371 (c)(1),
(2) Date: Dec. 18, 2017

(87) PCT Pub. No.: WO2016/205615

PCT Pub. Date: Dec. 22, 2016

(65) Prior Publication Data

US 2018/0372756 A1 Dec. 27, 2018

Related U.S. Application Data

(60) Provisional application No. 62/180,988, filed on Jun. 17, 2015.

(51) Int. Cl.
*C07K 14/47* (2006.01)
*C12N 15/62* (2006.01)
(Continued)

(52) U.S. Cl.
CPC ....... *G01N 33/6875* (2013.01); *A61K 35/761* (2013.01); *C07K 14/4703* (2013.01);
(Continued)

(58) Field of Classification Search
None
See application file for complete search history.

(56) References Cited

U.S. PATENT DOCUMENTS 5,399,363 A 3/1995 Liversidge et al.
5,466,468 A 11/1995 Schneider et al.
(Continued)

FOREIGN PATENT DOCUMENTS

WO 2009008529 A1 1/2009
WO 2010111587 A1 9/2010
WO 2013169793 A2 2/2014

OTHER PUBLICATIONS

Daniels et al., Expression of Multiple Transgenes from a Single Construct Using Viral 2A Peptides in *Drosophila*. PLoS One, 2014, 9:1-10 (Year: 2014).*

(Continued)

*Primary Examiner* — Arthur S Leonard
(74) *Attorney, Agent, or Firm* — Johns Hopkins Technology Ventures

(57) ABSTRACT

Chimeric proteins comprising an N-terminal domain derived from an N-terminal nucleotide binding domain of TDP-43 and a C-terminal domain derived from a splicing repressor are described. These proteins may be administered to a subject to treat or prevent disease manifesting TDP-43 proteinopathy such as inclusion body myocytosis, amyotrophic lateral sclerosis (ALS), or frontotemporal dementia (FTD).

1 Claim, 6 Drawing Sheets

Specification includes a Sequence Listing.

(51) Int. Cl.

| | |
|---|---|
| ***G01N 33/68*** | (2006.01) |
| ***C12Q 1/6883*** | (2018.01) |
| ***A61K 35/761*** | (2015.01) |
| *A61K 38/00* | (2006.01) |

(52) U.S. Cl.

CPC ....... *C12Q 1/6883* (2013.01); *G01N 33/6872* (2013.01); *A01K 2227/105* (2013.01); *A01K 2267/0356* (2013.01); *A61K 38/00* (2013.01); *C07K 2319/00* (2013.01); *C12Q 2600/158* (2013.01); *G01N 2333/4704* (2013.01); *G01N 2800/28* (2013.01)

(56) References Cited

U.S. PATENT DOCUMENTS

| | | | | |
|---|---|---|---|---|
| 5,543,158 | A | 8/1996 | Gref et al. | |
| 5,580,579 | A | 12/1996 | Ruddy et al. | |
| 5,629,001 | A | 5/1997 | Michael et al. | |
| 5,641,515 | A | 6/1997 | Ramtoola | |
| 5,725,871 | A | 3/1998 | Ilium | |
| 5,756,353 | A | 5/1998 | Debs | |
| 5,780,045 | A | 7/1998 | McQuinn et al. | |
| 5,792,451 | A | 8/1998 | Sarubbi et al. | |
| 5,804,212 | A | 9/1998 | Ilium | |
| 6,613,308 | B2 | 9/2003 | Bartus et al. | |
| 8,969,005 | B2 * | 3/2015 | Gitler .................. | C12Q 1/6883 435/6.11 |
| 2009/0263824 | A1 | 10/2009 | Lee et al. | |
| 2011/0053857 | A1 * | 3/2011 | Lindquist ........... | C12N 15/1079 514/17.7 |
| 2012/0237499 | A1 | 9/2012 | Gitler et al. | |
| 2013/0219534 | A1 * | 8/2013 | Wong .................... | A61K 31/00 800/18 |

OTHER PUBLICATIONS

Wagner et al., Polypyrimidine Tract Binding Protein Antagonizes Exon Definition. Molecular and Cellular Biology, 2001, 21:3281-3288 (Year: 2001).*

NCBI Reference Sequence: NP_597709.3. ribonucleoprotein PTB-binding 1 isoform 1 [*Homo sapiens*]. pp. 1-4. First submitted 2001. (Year: 2001).*

NCBI Reference Sequence: I38977. TAR DNA-binding protein-43—human. p. 1. First submitted 1999. (Year: 1999).*

Vance, et al., Mutations in FUS, an RNA processing protein, cause familial amyotrophic lateral sclerosis type 6. Science. 323, 1208-1211 (2009).

Johnson, et al., Mutations in the Matrin 3 gene cause familial amyotrophic lateral sclerosis. Nat. Neurosci. 17, 664-6 (2014).

Sawaya, et al., Microsatellite Tandem Repeats Are Abundant in Human Promoters and Are Associated with Regulatory Elements. PLoS One. 8 (2013).

Josephs, et al., Staging TDP-43 pathology in Alzheimer's disease. Acta Neuropathol. 127, 441-450 (2014).

Weihl, et al., TDP-43 accumulation in inclusion body myopathy muscle suggests a common pathogenic mechanism with frontotemporal dementia. J. Neurol. Neurosurg. Psychiatry. 79, 1186-1189 (2008).

Ying, et al., The ground state of embryonic stem cell self-renewal. Nature. 453, 519-523 (2008).

Trapnell, et al., Differential gene and transcript expression analysis of RNA-seq experiments with TopHat and Cufflinks. Nat. Protoc. 7, 562-78 (2012).

Goecks, et al., Galaxy: a comprehensive approach for supporting accessible, reproducible, and transparent computational research in the life sciences. Genome Biol. 11, R86 (2010).

Kent, et al., The human genome browser at UCSC. Genome Res. 12, 996-1006 (2002).

Tripathi, et al., Tar DNA-binding protein-43 (TDP-43) regulates axon growth in vitro and in vivo. Neurobiology of Disease, 65, 25-34, 2014.

Lagier-Tourenne, et al., TDP-43 and FUS/TLS: emerging roles in RNA processing and neurodegeneration. Human Molecular Genetics, 19, R46-64, 2010.

He, et al., TDP-43 suppresses CGG repeat-induced neurotoxicity through interactions with HnRNP A2/B1. Human Molecular Genetics, 23, 5036-5051, 2014.

Janssens, et al., Pathological mechanisms underlying TDP-43 driven neurodegeneration in FTLD-ALS spectrum disorders. Human Molecular Genetics, 22, R77-R87, 2013.

Fiesel, et al., TDP-43 and FUS/TLS: cellular functions and implications for neurodegeneration. FEBS Journal, 278, 3550-3568, 2011.

Ling, et al., TDP-43 repression of nonconserved cryptic exons is compromised in ALS-ITD. Science, 349, 650-655, 2015.

Ling, et al., Converging mechanisms in ALS and FTD: disrupted RNA and protein homeostasis. Neuron. 79, 416-38 (2013).

Neumann, et al., Ubiquitinated TDP-43 in frontotemporal lobar degeneration and amyotrophic lateral sclerosis. Science. 314, 130-3 (2006).

Lee, et al., Gains or losses: molecular mechanisms of TDP43-mediated neurodegeneration. Nat. Rev. Neurosci. 13, 38-50 (2012).

Qin, et al., TDP-43 N terminus encodes a novel ubiquitin-like fold and its unfolded form in equilibrium that can be shifted by binding to ssDNA. Proc. Natl. Acad. Sci., 201413994 (2014).

Pesiridis, et al., Mutations in TDP-43 link glycine-rich domain functions to amyotrophic lateral sclerosis. Hum. Mol. Genet. 18,156-162 (2009).

Watts, et al., Inclusion body myopathy associated with Paget disease of bone and frontotemporal dementia is caused by mutant valosin-containing protein. Nat. Genet. 36, 377-381 (2004).

Johnson, et al., Exome Sequencing Reveals VCP Mutations as a Cause of Familial ALS. Neuron. 68, 857-864 (2010).

Cruts, et al., Null mutations in progranulin cause ubiquitin-positive frontotemporal dementia linked to chromosome 17q21. Nature. 442, 920-924 (2006).

Baker, et al., Mutations in progranulin cause tau-negative frontotemporal dementia linked to chromosome 17. Nature. 442, 916-919 (2006).

Maruyama, et al., Mutations of optineurin in amyotrophic lateral sclerosis. Nature. 465, 223-226 (2010).

Elden, et al., Ataxin-2 intermediate-length polyglutamine expansions are associated with increased risk for ALS. Nature. 466, 1069-1075 (2010).

Fecto, et al., SQSTM1 mutations in familial and sporadic amyotrophic lateral sclerosis. Arch. Neurol. 68, 1440-1446 (2011).

Deng, et al., Mutations in UBQLN2 cause dominant X-linked juvenile and adult-onset ALS and ALS/dementia. Nature. 477, 211-5 (2011).

Wu, et al., Mutations in the profilin 1 gene cause familial amyotrophic lateral sclerosis. Nature. 488 (2012), pp. 499-503.

Dejesus-Hernandez, et al., Expanded GGGGCC hexanucleotide repeat in noncoding region of C9ORF72 causes chromosome 9p-linked FTD and ALS. Neuron. 72, 245-56 (2011).

Renton, et al., A hexanucleotide repeat expansion in C9ORF72 is the cause of chromosome 9p21-linked ALS-FTD. Neuron. 72, 257-68 (2011).

Ng, et al., Frontotemporal dementia: a bridge between dementia and neuromuscular disease. Ann. N. Y. Acad. Sci., 1-23 (2014).

Wu, et al., TDP-43, a neuro-pathosignature factor, is essential for early mouse embryogenesis. Genesis. 48, 56-62 (2010).

Sephton, et al., TDP-43 is a developmentally regulated protein essential for early embryonic development. J. Biol. Chem. 285, 6826-34 (2010).

Chiang, et al., Deletion of TDP-43 down-regulates Tbc1d1, a gene linked to obesity, and alters body fat metabolism. Proc. Natl. Acad. Sci. U. S. A. 107, 16320-4 (2010).

Wu, et al., Targeted depletion of TDP-43 expression in the spinal cord motor neurons leads to the development of amyotrophic lateral sclerosis-like phenotypes in mice. J. Biol. Chem. 287, 27335-27344 (2012).

Yang, et al., Partial loss of TDP-43 function causes phenotypes of amyotrophic lateral sclerosis. Proc. Natl. Acad. Sci. U. S. A. 111, E1121-9 (2014).

(56) References Cited

OTHER PUBLICATIONS

Feiguin, et al., Depletion of TDP-43 affects *Drosophila* motoneurons terminal synapsis and locomotive behavior. FEBS Lett. 583, 1586-1592 (2009).
Schmid, et al., Loss of ALS-associated TDP-43 in zebrafish causes muscle degeneration, vascular dysfunction, and reduced motor neuron axon outgrowth. Proc. Natl. Acad. Sci. U. S. A. 110, 4986-91 (2013).
Ayala, et al., TDP-43 regulates its mRNA levels through a negative feedback loop. EMBO J. 30, 277-288 (2011).
Avendano-Vazquez, et al., Autoregulation of TDP-43 mRNA levels involves interplay between transcription, splicing, and alternative polyA site selection. Genes Dev. 26, 1679-84 (2012).
Kuo, et al., Structural insights into TDP-43 in nucleic-acid binding and domain interactions. Nucleic Acids Res. 37, 1799-808 (2009).
Lukavsky, et al., Molecular basis of UG-rich RNA recognition by the human splicing factor TDP-43. Nat. Struct. Mol. Biol. 20, 1443-9 (2013).
Moore, et al., Mapping Argonaute and conventional RNA-binding protein interactions with RNA at single-nucleotide resolution using HITS-CLIP and CIMS analysis. Nat. Protoc. 9, 263-93 (2014).
Tollervey, et al., Characterizing the RNA targets and position-dependent splicing regulation by TDP-43. Nat. Neurosci. 14, 452-8 (2011).
Polymenidou, et al., Long pre-mRNA depletion and RNA missplicing contribute to neuronal vulnerability from loss of TDP-43. Nat. Neurosci. 14, 459-68 (2011).
Zhang et al. The dual functions of the extreme N-terminus of TDP-43 in regulating its biological activity and inclusion formation. Hum. Mol. Genet. 22, 3112-22 (2013).
Ayala, et al., Human, *Drosophila*, and *C. elegans* TDP43: nucleic acid binding properties and splicing regulatory function. J. Mol. Biol. 348, 575-88 (2005).
D'Ambrogio, et al., Functional mapping of the interaction between TDP-43 and hnRNP A2 in vivo. Nucleic Acids Res. 37, 4116-26 (2009).
Nonaka, et al., Prion-like Properties of Pathological TDP-43 Aggregates from Diseased Brains. Cell Rep. 4, 124-134 (2013).
Gromak, et al., The PTB interacting protein raver1 regulates α-tropomyosin alternative splicing. EMBO . . . 22, 6256-64 (2003).
Rideau, et al., A peptide motif in Raver1 mediates splicing repression by interaction with the PTB RRM2 domain. Nat. Struct. Mol. Biol. 13, 839-48 (2006).
Fu, et al., Context-dependent control of alternative splicing by RNA-binding proteins. Nat. Rev. Genet. 15, 689-701 (2014).
Klionsky, et al., A unified nomenclature for yeast autophagy-related genes. Dev. Cell. 5 (2003), pp. 539-545.
Marino, et al., Autophagy is essential for mouse sense of balance. J. Clin. Invest. 120, 2331-2344 (2010).
Bischoff, et al., Co-activation of RanGTPase and inhibition of GTP dissociation by Ran-GTP binding protein RanBP1. EMBO J. 14, 705-715 (1995).
Hayashi, et al., RanBP1, a Ras-like nuclear G protein binding to Ran/TC4, inhibits RCC1 via Ran/TC4. MGG Mol. Gen. Genet. 247, 661-669 (1995).
Alami, et al., Axonal transport of TDP-43 mRNA granules is impaired by ALS-causing mutations. Neuron. 81, 536-43 (2014).
Kim, et al., Mutations in prion-like domains in hnRNPA2B1 and hnRNPA1 cause multisystem proteinopathy and ALS. Nature. 495, 467-73 (2013).
Kwiatkowski, et al., Mutations in the FUS/TLS gene on chromosome 16 cause familial amyotrophic lateral sclerosis. Science. 323, 1205-1208 (2009).

* cited by examiner

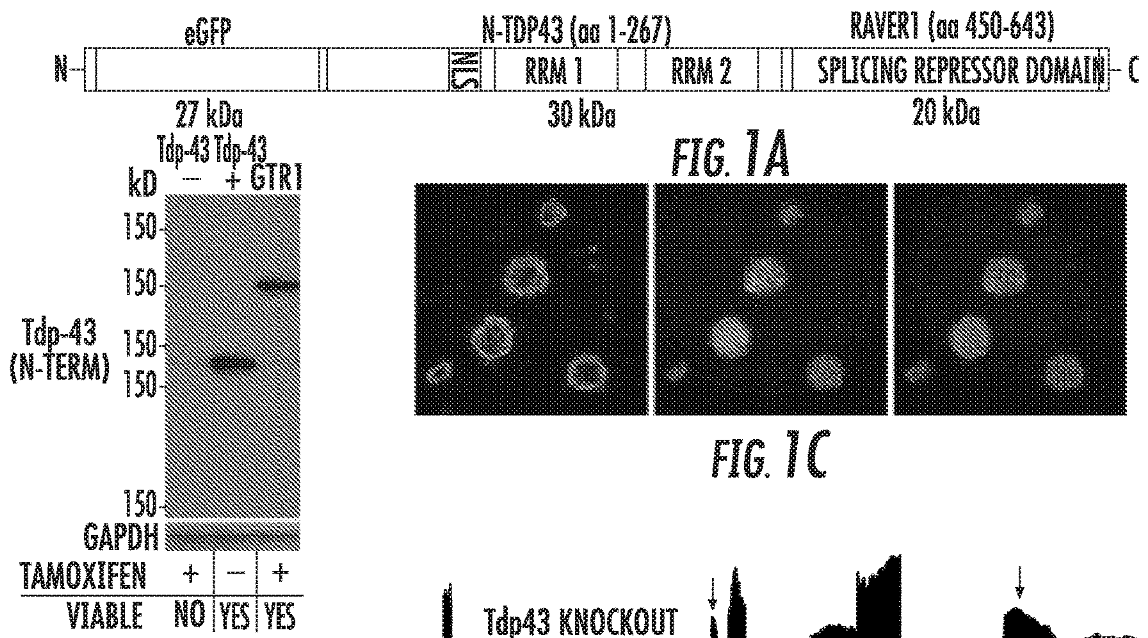
FIG. 1A
FIG. 1B
FIG. 1C
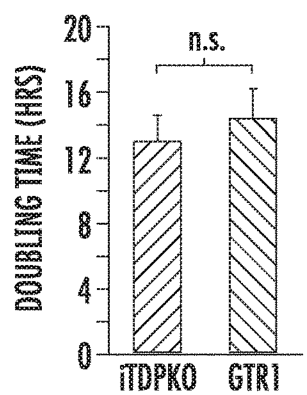
FIG. 1D
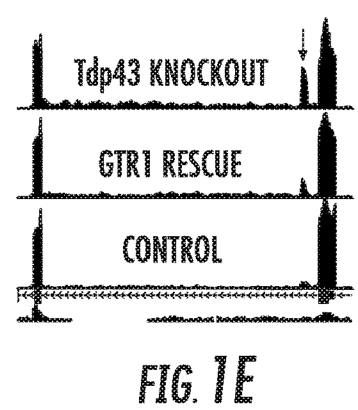
FIG. 1E
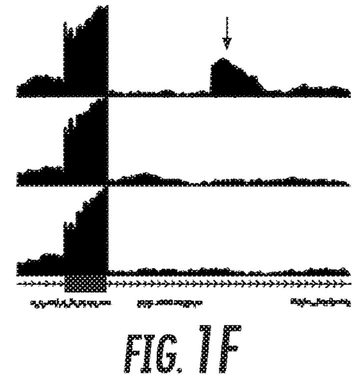
FIG. 1F
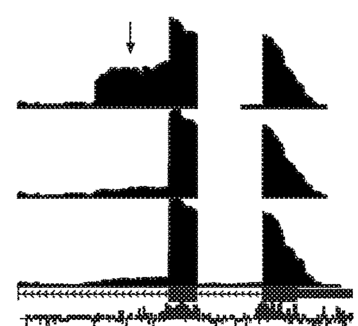
FIG. 1G
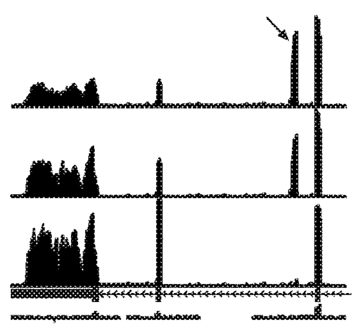
FIG. 1H
TOP DOWNREGULATED TOP UPREGULATED FOLD CHANGE
Tdp-43 KNOCKOUT
GTR1 RESCUE
CONTROL
+5
-5
FIG. 1I

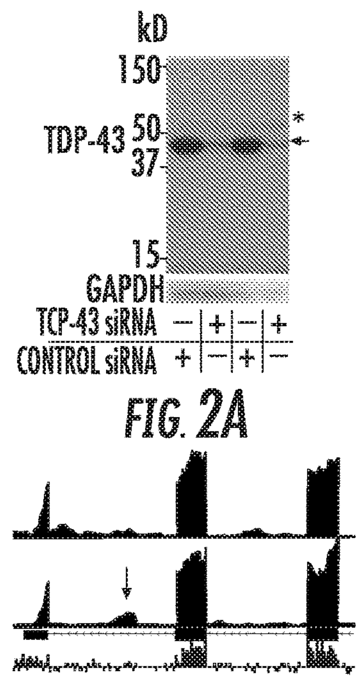
FIG. 2A
FIG. 2C
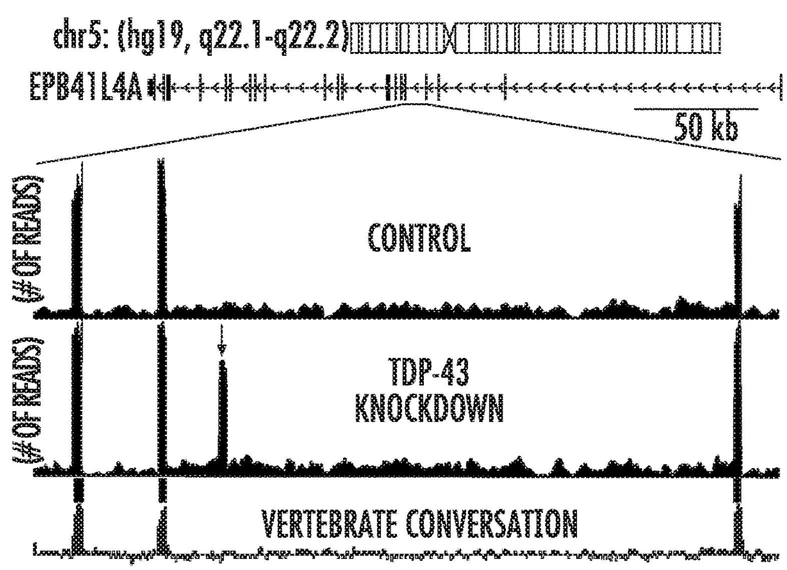
FIG. 2B
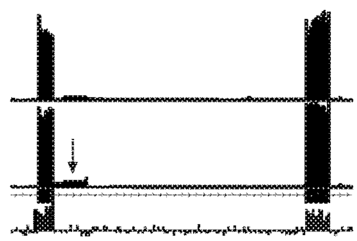
FIG. 2D
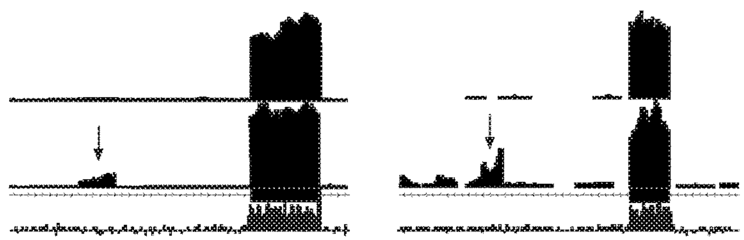
FIG. 2E
FIG. 2F

| GENE | HUMAN (hg19) GENOMIC SEQUENCE | | | |
|---|---|---|---|---|
| | 5' UPSTREAM (INTRON) | 5' CRYPTIC EXON | 3' CRYPTIC EXON | 5' DOWNPSTREAM (INTRON) |
| ITPR3 | GGUUGUGAAUGUGGGUGUCAGCCUGUAUGUUUGUGACAG | CUCUCUGACACUAUGUGUG | CACCCCACCUGACCCCCAG | CUCCUGCAUGAAGAGCAACAAGUACCUGACAGUGAAC |
| COL4A6 | AUGUGUAUGUGUGUUUUCCCUGUGAAUGUCUGCUACUAG | GUGCAGUGAUGGAGUCCUG | CGAGAUGAGCUCUUGCAG | GUUUGUCAGCCUGUAGGUUUCUGGGCCCACUCUGGCCC |
| RANBP1 | UGUGUUUGUUGAAUUUAAAACCAGAAAUACGUUUUUCAG | ACGUGCCUCUGAACUCAGA | GCUGGGCUCGGGACGAGGA | GUGAGUGCUGCAGGGCGAGGGGUGCUGUUGUGUGUGUGU |
| PFKP | UGUGUUAAUCUGUGAGUCACUUUGAGUCACUUGUUAAUAG | AAAUAAUCCAAAUCGGUCC | AUGUGAACGGAGAGUUGAA | GUGCGUAUGUGUAUCAGUGAGUCUGUGUUUCUGUGUGUG |
| ZFP91 | AGUUAGUAGCCUUUUUCUUAGUUUCCCUCUGUUUUUCAG | GCAAACAGAAGAAGAUCAG | UCCCAAUCCUUCAAAAGAA | GUAUGUUACUGAUUAUUGUGUGUGUGUGUGUGUGU |
| ST5 | AUUUAUGAUUUAUAUGUCUAUUGUAUUCACCCUACAG | AGUGGAAGCUCCUUGAGGA | UGUCCUGCCUGGAGAGAG | GUAGGUGUGUGUGUGUGUGUGUGUGUGUGCGCGCGCG |
| NSMCE4A | UGUUUCUUUUCCUGUCCCAUUCUGUUUUGCCUUCCUCAG | CUCCCUGCUAUUGGUCCAC | UGCUGGUCUCCAGUCUGGC | GUGUGUUGUGUGUGAGUGAGUGAGUGAGAGAGAUCCCAG |
| MUC16 | CUGGGGAGGUGUAUGCUGCUAUUUCUGCUUUAACUGUAG | GCAAACUGGGGCUCAGUGA | GGACUUGAGUUCCUGCCCA | GUGAGUAUGCGUGUGGAUAAGUGUGUGAUUAUGUGUCUG |
| PARP6 | GUGGACAUUGACCUCCACAUCAACAUCAGUUCCUCGAU | GUAAGUGGGGCUAGUACCU... | AGACCAUCAGCAGACAGUC | GUGUGUACUGUCAUGUGCAUGUGUGUGUCAUAUAGGGA |
| KRT7 | CGCACAGCUGCUGAGAAUGAGUUUGUGGUGCUGAAGAAG | GUGAGUGGGAAAGACAGGC... | UGCACAGCCUGUCCUGUGC | GUGCGUGUAUGUGUGUGUGUGUGUGUGUGUGUGUG |
| TRAPPC12 | UCUGCACAGUGAGGCCAUGCCAGCUGCAGCUCGGGGAGU | GCGUUAGCCAGGAGCAAGC... | UGAGCUGAACGUGUGUGAC | GUGUGUAUGUGUGUGGUGUGUGGAUGUUGGGUGUGCAUG |
| XPO4 | UGUGCAGCUCCUUGUCACUUUGGUGGAAAGAAGAGAAAG | GUUAGCCCAUUGUUGGAGG... | UGUGUGUGUAUGUGUGUCC | GUGAGAAACUCUUUUUCACUUCUUAGUGUAGUCCUUUGA |

FIG. 2G

SEQUENCE LISTING

```
<160> NUMBER OF SEQ ID NOS: 38

<210> SEQ ID NO 1
<211> LENGTH: 22
<212> TYPE: PRT
<213> ORGANISM: Homo sapiens

<400> SEQUENCE: 1
```

```
Ala Met Cys Asp Trp Lys Val Ala Pro Thr Pro Arg Arg Ala Trp Leu
1               5                   10                  15

Val Arg His Lys Pro Gly
            20


<210> SEQ ID NO 2
<211> LENGTH: 63
<212> TYPE: PRT
<213> ORGANISM: Homo sapiens

<400> SEQUENCE: 2

Ala Arg Val Cys Val Cys Thr Glu Leu Arg Val Arg Asp Leu Trp Met
1               5                   10                  15

Leu Cys Val Leu Cys Val Pro Gly Ser Ala Phe Thr Asp Met Phe Leu
            20                  25                  30

Arg Lys Met Trp Glu Pro His Leu Cys Pro Gln Pro Gln Ala Pro Gly
        35                  40                  45

Leu Leu Trp Glu Leu Gly Ser Gly Arg Leu Ser Gly Asp Ser Gly
    50                  55                  60


<210> SEQ ID NO 3
<211> LENGTH: 26
<212> TYPE: PRT
<213> ORGANISM: Homo sapiens

<400> SEQUENCE: 3

Ser Asp Ile Glu Ser Pro Tyr Lys Thr Glu Val Thr Lys Gly Gln Ala
1               5                   10                  15

Glu Val Cys Glu Ser Val Cys Ala Tyr Val
            20                  25


<210> SEQ ID NO 4
<211> LENGTH: 46
<212> TYPE: PRT
<213> ORGANISM: Homo sapiens

<400> SEQUENCE: 4

Glu Pro Thr Ile Trp Phe Gly Lys Gly His Ser Gly Met Leu Ala Ser
1               5                   10                  15

Glu Gly Arg Glu Ala Val Leu Thr Arg Leu His Glu Ser Glu Arg Val
            20                  25                  30

Arg Lys Gln Glu Arg Glu Arg Asp Thr Glu Glu Arg Arg Glu
        35                  40                  45


<210> SEQ ID NO 5
<211> LENGTH: 268
<212> TYPE: PRT
<213> ORGANISM: Homo sapiens

<400> SEQUENCE: 5

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
```

```
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg
            260                 265


<210> SEQ ID NO 6
<211> LENGTH: 194
<212> TYPE: PRT
<213> ORGANISM: Homo sapiens

<400> SEQUENCE: 6

Gly Lys Pro Pro Pro Leu Leu Pro Ser Val Leu Gly Pro Ala Gly Gly
1               5                   10                  15

Asp Arg Glu Ala Leu Gly Leu Gly Pro Pro Ala Ala Gln Leu Thr Pro
            20                  25                  30

Pro Pro Ala Pro Val Gly Leu Arg Gly Ser Gly Leu Arg Gly Leu Gln
        35                  40                  45

Lys Asp Ser Gly Pro Leu Pro Thr Pro Pro Gly Val Ser Leu Leu Gly
    50                  55                  60

Glu Pro Pro Lys Asp Tyr Arg Ile Pro Leu Asn Pro Tyr Leu Asn Leu
65                  70                  75                  80

His Ser Leu Leu Pro Ala Ser Asn Leu Ala Gly Lys Glu Ala Arg Gly
                85                  90                  95

Trp Gly Gly Ala Gly Arg Ser Arg Arg Pro Ala Glu Gly Pro Pro Thr
            100                 105                 110

Asn Pro Pro Ala Pro Gly Gly Gly Ser Ser Ser Ser Lys Ala Phe Gln
        115                 120                 125

Leu Lys Ser Arg Leu Leu Ser Pro Leu Ser Ser Ala Arg Leu Pro Pro
    130                 135                 140

Glu Pro Gly Leu Ser Asp Ser Tyr Ser Phe Asp Tyr Pro Ser Asp Met
145                 150                 155                 160

Gly Pro Arg Arg Leu Phe Ser His Pro Arg Glu Pro Ala Leu Gly Pro
                165                 170                 175
```

```
His Gly Pro Ser Arg His Lys Met Ser Pro Pro Pro Ser Gly Phe Gly
            180                 185                 190

Glu Arg


<210> SEQ ID NO 7
<211> LENGTH: 307
<212> TYPE: PRT
<213> ORGANISM: Homo sapiens

<400> SEQUENCE: 7

Gly Lys Pro Pro Pro Leu Leu Pro Ser Val Leu Gly Pro Ala Gly Gly
1               5                   10                  15

Asp Arg Glu Ala Leu Gly Leu Gly Pro Pro Ala Ala Gln Leu Thr Pro
            20                  25                  30

Pro Pro Ala Pro Val Gly Leu Arg Gly Ser Gly Leu Arg Gly Leu Gln
        35                  40                  45

Lys Asp Ser Gly Pro Leu Pro Thr Pro Pro Gly Val Ser Leu Leu Gly
    50                  55                  60

Glu Pro Pro Lys Asp Tyr Arg Ile Pro Leu Asn Pro Tyr Leu Asn Leu
65                  70                  75                  80

His Ser Leu Leu Pro Ala Ser Asn Leu Ala Gly Lys Glu Ala Arg Gly
                85                  90                  95

Trp Gly Gly Ala Gly Arg Ser Arg Arg Pro Ala Glu Gly Pro Pro Thr
            100                 105                 110

Asn Pro Pro Ala Pro Gly Gly Gly Ser Ser Ser Ser Lys Ala Phe Gln
        115                 120                 125

Leu Lys Ser Arg Leu Leu Ser Pro Leu Ser Ser Ala Arg Leu Pro Pro
    130                 135                 140

Glu Pro Gly Leu Ser Asp Ser Tyr Ser Phe Asp Tyr Pro Ser Asp Met
145                 150                 155                 160

Gly Pro Arg Arg Leu Phe Ser His Pro Arg Glu Pro Ala Leu Gly Pro
                165                 170                 175

His Gly Pro Ser Arg His Lys Met Ser Pro Pro Pro Ser Gly Phe Gly
            180                 185                 190

Glu Arg Ser Ser Gly Gly Ser Gly Gly Gly Pro Leu Ser His Phe Tyr
        195                 200                 205

Ser Gly Ser Pro Thr Ser Tyr Phe Thr Ser Gly Leu Gln Ala Gly Leu
    210                 215                 220

Lys Gln Ser His Leu Ser Lys Ala Ile Gly Ser Ser Pro Leu Gly Ser
225                 230                 235                 240

Gly Glu Gly Leu Leu Gly Leu Ser Pro Gly Pro Asn Gly His Ser His
                245                 250                 255

Leu Leu Lys Thr Pro Leu Gly Gly Gln Lys Arg Ser Phe Ala His Leu
            260                 265                 270

Leu Pro Ser Pro Glu Pro Ser Pro Glu Gly Ser Tyr Val Gly Gln His
        275                 280                 285

Ser Gln Gly Leu Gly Gly His Tyr Ala Asp Ser Tyr Leu Lys Arg Lys
    290                 295                 300

Arg Ile Phe
305


<210> SEQ ID NO 8
<211> LENGTH: 38
<212> TYPE: PRT
<213> ORGANISM: Homo sapiens
```

<400> SEQUENCE: 8

Gln Thr Glu Glu Asp Gln Ile Ser Phe Pro Ser Ser Asn Ile Ser Gln
1 5 10 15

Ser Phe Lys Arg Asn Val Arg Ser Val Asp Leu Leu Val Asp Lys Arg
20 25 30

His Leu Leu Ile Gly Thr
35

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tgtgtctgga tgtgagcgtg 20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tctagggaca ggttcaggac g 21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
agtggacatg tggtggtaag aa 22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcttcaaaga atgacacgcc a 21

<210> SEQ ID NO 13
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgtctgaat atattcgggt aaccgaagat gagaacgatg agcccattga aataccatcg 60
gaagacgatg ggacggtgct gctctccacg gttacagccc agtttccagg ggcgtgtggg 120
cttcgctaca ggaatccagt gtctcagtgt atgagaggtg tccggctggt agaaggaatt 180

```
ctgcatgccc cagatgctgg ctggggaaat ctggtgtatg ttgtcaacta tccaaaagat    240

aacaaaagaa aaatggatga gacagatgct tcatcagcag tgaaagtgaa aagagcagtc    300

cagaaaacca gcgacctgat tgtcctgggt ctcccatgga aacaaccgaa acaggacctg    360

aaagagtatt ttagtacctt tggagaagtt cttatggtgc aggtcaagaa ggacttgaag    420

acaggacata gcaaggggtt tggctttgtt cgttttacgg aatatgaaac acaagtgaaa    480

gtaatgtcac agcgacatat gatagatgga cgatggtgtg actgcaaact tcctaattct    540

aagcaaagcc aagatgagcc tttgagaagc agaaaagtgt ttgtggggcg ctgtactgag    600

gacatgactg aggatgagct gcgggagttc ttctctcagt acggggatgt gatggatgtc    660

ttcatcccca agccattcag ggcctttgcc tttgttacat ttgcagatga tcagattgcg    720

cagtctcttt gtggagagga cttgatcatt aaaggaatca gcgttcatat atccaatgcc    780

gaacctaagc acaatagcaa tagaacgcgt ggcaagcctc cacctctgct gccatccgtg    840

cttggacctg ctggaggtga cagagaggct ctgggcttgg gtcctccagc agctcagctc    900

actcctccac cagcacctgt gggactccga ggctctggcc tcagaggcct ccagaaagac    960

agtgggcctc tgccgacgcc tcctggagtc tcactgctgg gagaacctcc taaggactac   1020

cggattccac tgaatcccta cctgaaccta cacagcctgc tccctgccag caacctggcg   1080

ggtaaggaag ctagaggctg gggaggcgcc ggaagaagcc gccgcccagc tgagggccct   1140

ccaactaacc ctccagcacc tggaggtggc agcagcagca gcaaagcctt ccagctcaag   1200

tctcgcctgc tcagtccact cagcagcgca cgcctgcctc ctgaaccagg actgtctgac   1260

agctacagct tcgactatcc ctcggacatg ggacctagac ggctcttcag ccacccacgg   1320

gaaccagccc ttgggcctca cggacccagc cgacacaaga tgtctcctcc accaagtggc   1380

ttcggcgaac ggtag                                                    1395
```

```
<210> SEQ ID NO 14
<211> LENGTH: 58
<212> TYPE: RNA
<213> ORGANISM: Homo sapiens

<400> SEQUENCE: 14

gguugugaau guggguguca gccuguaugu uugugacagg ugucugacac uaugugug      58


<210> SEQ ID NO 15
<211> LENGTH: 58
<212> TYPE: RNA
<213> ORGANISM: Homo sapiens

<400> SEQUENCE: 15

caccccaccu gacccccagc uccugcacau gaagagcaac aaguaccuga cagugaac      58


<210> SEQ ID NO 16
<211> LENGTH: 58
<212> TYPE: RNA
<213> ORGANISM: Homo sapiens

<400> SEQUENCE: 16

auguguaugu guguuuuccc ugugaauguc ugcuacuagg ugcagugaug gaguccug      58


<210> SEQ ID NO 17
<211> LENGTH: 58
<212> TYPE: RNA
<213> ORGANISM: Homo sapiens
```

<400> SEQUENCE: 17
cgaagaugag cucuugcagg uuugucagcc uguagguuuc ugggcccacu cuggcccc 58

<210> SEQ ID NO 18
<211> LENGTH: 58
<212> TYPE: RNA
<213> ORGANISM: Homo sapiens

<400> SEQUENCE: 18
uguguuuguu gaauuuaaaa ccagaaauac guuuuucaga cgugccucug aacucaga 58

<210> SEQ ID NO 19
<211> LENGTH: 58
<212> TYPE: RNA
<213> ORGANISM: Homo sapiens

<400> SEQUENCE: 19
gcugggcucg ggacgaggag ugagugcugc agggcgaggg ggugcugugu gugugugu 58

<210> SEQ ID NO 20
<211> LENGTH: 58
<212> TYPE: RNA
<213> ORGANISM: Homo sapiens

<400> SEQUENCE: 20
uguguuaauc ugugagucac uuugaguacu uguuaauaga aauaauccaa aucggugc 58

<210> SEQ ID NO 21
<211> LENGTH: 58
<212> TYPE: RNA
<213> ORGANISM: Homo sapiens

<400> SEQUENCE: 21
augugaacgg agaguugaag ugcguaugug uaucagugag ucuguguuuc ugugugug 58

<210> SEQ ID NO 22
<211> LENGTH: 58
<212> TYPE: RNA
<213> ORGANISM: Homo sapiens

<400> SEQUENCE: 22
aguuaguagc cuuuuucuua guuucccucu guuuuucagg caaacagaag aagaucag 58

<210> SEQ ID NO 23
<211> LENGTH: 58
<212> TYPE: RNA
<213> ORGANISM: Homo sapiens

<400> SEQUENCE: 23
ucccaauccu ucaaaagaag uauguuacug auuauugugu gugugugugu gugugugu 58

<210> SEQ ID NO 24
<211> LENGTH: 58
<212> TYPE: RNA
<213> ORGANISM: Homo sapiens

<400> SEQUENCE: 24
auuuaugaga uuuauauguc uauuguauuc acccuacaga guggaagcuc cuugagga 58

<210> SEQ ID NO 25
<211> LENGTH: 58
<212> TYPE: RNA
<213> ORGANISM: Homo sapiens

<400> SEQUENCE: 25 gugucugcc uggagagagg uaggugugug ugugugugug ugugugugug cgcgcgcg 58

<210> SEQ ID NO 26
<211> LENGTH: 58
<212> TYPE: RNA
<213> ORGANISM: Homo sapiens

<400> SEQUENCE: 26
uguuucuuuu ccugucccau ucuguuuugc cuuccucagc ucccugcuau ugguccac 58

<210> SEQ ID NO 27
<211> LENGTH: 58
<212> TYPE: RNA
<213> ORGANISM: Homo sapiens

<400> SEQUENCE: 27
ugcuggucuc cagucugggg uguguugugu gugagugagu gagugagaga gaucccag 58

<210> SEQ ID NO 28
<211> LENGTH: 58
<212> TYPE: RNA
<213> ORGANISM: Homo sapiens

<400> SEQUENCE: 28
cuggggaggu guaugcugcu auuucugcuu uaacuguagg gaaacugggg cucaguga 58

<210> SEQ ID NO 29
<211> LENGTH: 58
<212> TYPE: RNA
<213> ORGANISM: Homo sapiens

<400> SEQUENCE: 29
ggacuugagu uccugcccag ugaguaugcg uguggauaag ugugugauua ugugucug 58

<210> SEQ ID NO 30
<211> LENGTH: 58
<212> TYPE: RNA
<213> ORGANISM: Homo sapiens

<400> SEQUENCE: 30
guggacauug accuccacau caacaucagc uuccucgaug uaaguggggc uaguaccu 58

<210> SEQ ID NO 31
<211> LENGTH: 58
<212> TYPE: RNA
<213> ORGANISM: Homo sapiens

<400> SEQUENCE: 31
agaccaucag cagacagugg uguguacugu caugugcaug ugugugucau auagggga 58

<210> SEQ ID NO 32
<211> LENGTH: 58
<212> TYPE: RNA
<213> ORGANISM: Homo sapiens

<400> SEQUENCE: 32
cgcacagcug cugagaauga guuuguggug cugaagaagg ugagugggaa agacaggc 58

<210> SEQ ID NO 33
<211> LENGTH: 58
<212> TYPE: RNA

```
<213> ORGANISM: Homo sapiens

<400> SEQUENCE: 33

ugcacagccu guccuguggg ugcguguaug ugugugugug ugugugugug ugugugug       58


<210> SEQ ID NO 34
<211> LENGTH: 58
<212> TYPE: RNA
<213> ORGANISM: Homo sapiens

<400> SEQUENCE: 34

ucugcacagu gaggccaugc cagcugcagc ucggggagug cguuagccag gagcaagc       58


<210> SEQ ID NO 35
<211> LENGTH: 58
<212> TYPE: RNA
<213> ORGANISM: Homo sapiens

<400> SEQUENCE: 35

ugagcugaac gugugugagg uguguaugug uguggugugu ggauguuggg ugugcaug       58


<210> SEQ ID NO 36
<211> LENGTH: 58
<212> TYPE: RNA
<213> ORGANISM: Homo sapiens

<400> SEQUENCE: 36

ugugcagcuc cuugucacuu ugguggaaag aagagaaagg uuagcccauu guuggagg       58


<210> SEQ ID NO 37
<211> LENGTH: 58
<212> TYPE: RNA
<213> ORGANISM: Homo sapiens

<400> SEQUENCE: 37

ugugugugua ugugugugggg ugagaaacuc uuuuucacuu cuuaguguag uccuuuga       58


<210> SEQ ID NO 38
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38

ugugugugug ugug                                                       14
```

TDP-43 IN DEGENERATIVE DISEASE

REFERENCE TO RELATED APPLICATIONS

This application is a 35 U.S.C. § 371 U.S. national entry of International Application PCT/US2016/038037, having an international filing date of Jun. 17, 2016, which claims the benefit of U.S. Provisional Application No. 62/180,988 filed on Jun. 17, 2015 that is hereby incorporated by reference for all purposes as if fully set forth herein.

STATEMENT OF GOVERNMENT INTEREST

This invention was made with government support under grant no. P50AG05146 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 14, 2017, is named P13621-03 SL.txt and is 15,606 bytes in size.

BACKGROUND OF THE INVENTION

It is well established that ALS, or amyotrophic lateral sclerosis, a fatal adult onset motor neuron disease characterized by selective loss of upper and lower motor neurons, and FTD, a common form of dementia characterized by a progressive deterioration in behavior, personality and/or language, share a common disease spectrum. Transactivation response element DNA-binding protein 43 (TDP-43, TARDBP), is a heterogeneous nuclear ribonucleoprotein (hnRNP) thought to provide the neuropathological link to establish such a disease spectrum. In sporadic ALS (~95%) and FTD-TDP (~45% of all FTD), TDP-43 clears from the nucleus and forms large ubiquitinated, cytoplasmic inclusions, termed TDP-43 proteinopathy. Missense mutations in TDP-43 are also linked to familial ALS, strongly supporting the idea that TDP-43 proteinopathy is central to the pathogenesis of sporadic disease. Moreover, numerous genetic mutations associated with familial ALS-FTD—VCP, GRN, OPTN, ATXN2, SQSTM1, UBQLN2, PFN1 and especially C9ORF72—result in TDP-43 proteinopathy, suggesting a convergent mechanism of neurodegeneration. Although it is hypothesized that nuclear clearing of TDP-43 reflects a loss-of-function, exactly how this RNA-binding protein contributes to neurodegeneration in ALS-FTD has remained elusive. Identified as an essential gene, Tdp-43 is also required for aspects of neuronal physiology in mice, fruit flies and zebrafish, supporting the notion that nuclear clearance of TDP-43 could underlie neurodegeneration in ALS-FTD. Interestingly, the level of TDP-43 protein is exquisitely maintained in the cell through an autoregulatory mechanism by which TDP-43 binds to the 3'UTR of its own mRNA. Collectively, this body of work underscores the importance of TDP-43 for normal cellular function and supports the notion that TDP-43 dysregulation could be a common final pathway in ALS-FTD. Thus, understanding the biological role of TDP-43 is critical for clarifying the pathogenesis of ALS-FTD and other human diseases that exhibit TDP-43 proteinopathy.

TDP-43's consensus binding motif has been identified as the 'UG' dinucleotide repeat. Using a high-throughput sequencing approach combined with cross-linking immunoprecipitation (HITS-CLIP), direct targets of TDP-43 were identified. Notably, TDP-43 was shown to regulate alternative splicing of a subset of conserved exons by binding to 'UG' rich domains within proximal intronic regions. However, the vast majority of TDP-43 was inexplicably mapped to repetitive elements deep within distal introns, locations where TDP-43 had no clear function. After analyzing the transcriptome of Tdp-43 knockout cells with high-depth RNA sequencing (RNA-seq), the present invention demonstrates that Tdp-43 binds to distal introns to suppress the splicing of cryptic exons, thereby maintaining the integrity of its target mRNAs. Sequence analysis of these cryptic exon sites reveals the presence of adjacent 'UG' dinucleotide rich domains, supporting the notion that these exons are direct targets of Tdp-43. Importantly, these cryptic exons are not conserved, often introduce premature stop codons and are generally disruptive. Moreover, we show that cell death associated with deletion of Tdp-43 is reversed when these non-conserved cryptic exons are suppressed. Finally, we demonstrate that this novel splicing mechanism is conserved in humans and that TDP-43 proteinopathy correlates with the presence of cryptic exons in brains of ALS-FTD. The present invention revealed a physiological function of TDP-43 that is critical for cell survival and strongly support the view that TDP-43 loss-of-function occurs in ALS-FTD. We therefore propose that suppression of TDP-43 associated cryptic exons is a promising therapeutic strategy for attenuating human diseases that exhibit TDP-43 proteinopathy.

SUMMARY OF THE INVENTION

One embodiment of the present invention is a method for detecting TDP-43 dysregulation comprising the steps of: obtaining a biological sample from a subject; and testing the biological sample with an immunoassay based on an antibody or antibodies raised against one or more protein translated from one or more cryptic exons. Detection of one or more cryptic exons indicates dysregulation of TDP-43. Suitable biological samples used in the present invention include CSF, blood, and skeletal muscle. Suitable antibodies used in the present invention, for example, are those capable of binding to one or more proteins selected from the group comprising SEQ ID NO: 1, SEQ ID NO: 2, SEQ ID NO: 3, SEQ ID NO: 4, and SEQ ID NO: 8.

Another embodiment of the present invention is a method for detecting TDP-43 dysregulation comprising the steps of: obtaining a biological sample from a subject; and testing the biological sample with one or more nucleic acid probes of cryptic exons, wherein detection of one or more cryptic exons indicates dysregulation of TDP-43. Suitable cryptic exons are selected from the group comprising ACSF2, AGRN, EPB41L4A, HDGFRP2, and ZFP91.

Another embodiment of the present invention is a chimeric protein comprising: an N-terminal domain derived from an N-terminal nucleotide binding domain of TDP-43; and a C-terminal domain derived from a splicing repressor. A suitable splicing repressor includes RAVER 1, or a functional part thereof. Examples of suitable C-terminal domains include SEQ ID NO: 6 and/or SEQ ID NO: 7. An example of a suitable N-terminal domain comprise the amino acids of SEQ ID NO: 5. An example of a suitable cDNA sequence that is capable of expressing a chimeric protein of the present invention is SEQ ID NO: 13.

Another embodiment of the present invention is the use of a chimeric protein comprising an N-terminal domain derived from an N-terminal nucleotide binding domain of TDP-43 and a C-terminal domain derived from a splicing repressor that is administered to a subject to treat or prevent disease manifesting TDP-43 proteinopathy. It is preferred that the N-terminal domain binds to TDP-43 binding sites such as a 'UG' dinucleotide repeat. A suitable C-terminal domain actively represses splicing.

Another embodiment of the present invention is the use of a nucleic acid sequence capable of expressing a chimeric protein comprising an N-terminal domain derived from an N-terminal nucleotide binding domain of TDP-43 and a C-terminal domain derived from a splicing repressor that is administered to a subject to treat or prevent a disease manifesting TDP-43 proteinopathy. Chimera proteins of the present invention, or nucleic acids that express chimeria proteins of the present invention, such as viruses used in gene therapy, are suitable for treating or preventing disease manifesting TDP-43 such as inclusion body myocytosis, amyotrophic lateral sclerosis (ALS), or frontotemporal dementia (FTD).

Another embodiment of the present invention is the use of a virus comprising a nucleic acid capable of expressing a chimeric protein comprising an N-terminal domain derived from an N-terminal nucleotide binding domain of TDP-43: and a C-terminal domain derived from a splicing repressor that is administered to a subject to treat or prevent disease. A suitable virus that may be used in the present invention includes adenovirus, lentivirus, cytomegalovirus, or a combination thereof. A suitable promoter driving the expression of a chimeric protein of the present invention is derived from a CBh promoter. A chimeric protein of the present invention may be expressed from the cDNA sequence of SEQ ID NO: 13.

The term "ACSF2" is a gene having a cryptic exon (Hfg19 assembly) with human genome coordinates: chr17: 48,539,181-48,539,246. The amino acid sequence of the translated cryptic exon (SEQ ID NO: 1):

```
AMCDWKVAPTPRRAWLVRHKPG
```

The term "AGRN" is a gene having a cryptic exon (Hg19 assembly) with human genome coordinates: chr1:980,272-980,460. The amino acid sequence of the translated cryptic exon (SEQ ID NO: 2): ARVCVCTELRVRDLWMLCVLCVPGSAFTDMFLRK MWEPHLCPQPQAPGLLWELG SGRLSGDSG The term "EPB41L4A" is a gene having a cryptic exon (Hg19 assembly) with human genome coordinates: chr5: 111,602,907-111,602,981. The amino acid sequence of the translated exon (SEQ ID NO: 3):

```
SDIESPYKTEVTKGQAEVCESVCAYV
```

The term "HDGFRP2" is a gene having a cryptic exon (Hg19 assembly) with human genome coordinates: chr19: 4,492,012-4,492,149. The amino acid sequence of the translated cryptic exon (SEQ ID NO: 4):

```
EPTIWFGKGHSGMLASEGREAVLTRLHESERVRKQERERDTEERRE
```

The term "NTDP" or "N-terminus of TDP-43" refers to amino acids 1-268 of a human TDP-43 NCBI Protein Reference Sequence: NP_031401.1 having the amino acid sequence (SEQ ID NO: 5):

```
1MSEYIRVTEDENDEPIEIPSEDDGTVLLSTVTAQFPGACGLRYRNPVSQ
CMRGVRLVEGILHAPDAGWGNLVYVVNYPKDNKRKMDETDASSAVKVKRA
VQKTSDLIVLGLPWKTTEQDLKEYFSTFGEVLMVQVKKDLKTGHSKGFGF
VRFTEYETQVKVMSQRHMIDGRWCDCKLPNSKQSQDEPLRSRKVFVGRCT
EDMTEDELREFFSQYGDVMDVFIPKPFRAFAFVTFADDQIAQSLOGEDLI
IKGISVHISNAEPKHNSNR 268
```

The term "chimeric protein" includes a protein of the present invention having an N-terminal domain from an N-terminal nucleotide binding domain of TDP-43 that has TDP-43 binding activity and a C-terminal domain derived from a splicing repressor that is capable of repressing splicing. An example of a cDNA sequence encoding a chimeric protein is (SEQ ID NO: 13):

```
ATGTCTGAATATATTCGGGTAACCGAAGATGAGAACGATGAGCCCATTGA
AATACCATCGGAAGACGATGGGACGGTGCTGCTCTCCACGGTTACAGCCC
AGTTTCCAGGGGCGTGTGGGCTTCGCTACAGGAATCCAGTGTCTCAGTGT
ATGAGAGGTGTCCGGCTGGTAGAAGGAATTCTGCATGCCCCAGATGCTGG
CTGGGGAAATCTGGTGTATGTTGTCAACTATCCAAAAGATAACAAAAGAA
AAATGGATGAGACAGATGCTTCATCAGCAGTGAAAGTGAAAAGAGCAGTC
CAGAAAACCAGCGACCTGATTGTCCTGGGTCTCCCATGGAAAACAACCGA
ACAGGACCTGAAAGAGTATTTTAGTACCTTTGGAGAAGTTCTTATGGTGC
AGGTCAAGAAGGACTTGAAGACAGGACATAGCAAGGGGTTTGGCTTTGTT
CGTTTTACGGAATATGAAACACAAGTGAAAGTAATGTCACAGCGACATAT
GATAGATGGACGATGGTGTGACTGCAAACTTCCTAATTCTAAGCAAAGCC
AAGATGAGCCTTTGAGAAGCAGAAAAGTGTTTGTGGGGCGCTGTACTGAG
GACATGACTGAGGATGAGCTGCGGGAGTTCTTCTCTCAGTACGGGGATGT
GATGGATGTCTTCATCCCCAAGCCATTCAGGGCCTTTGCCTTTGTTACAT
TTGCAGATGATCAGATTGCGCAGTCTCTTTGTGGAGAGGACTTGATCATT
AAAGGAATCAGCGTTCATATATCCAATGCCGAACCTAAGCACAATAGCAA
TAGAACGCGTGGCAAGCCTCCACCTCTGCTGCCATCCGTGCTTGGACCTG
CTGGAGGTGACAGAGAGGCTCTGGGCTTGGGTCCTCCAGCAGCTCAGCTC
ACTCCTCCACCAGCACCTGTGGGACTCCGAGGCTCTGGCCTCAGAGGCCT
CCAGAAAGACAGTGGGCCTCTGCCGACGCCTCCTGGAGTCTCACTGCTGG
GAGAACCTCCTAAGGACTACCGGATTCCACTGAATCCCTACCTGAACCTA
CACAGCCTGCTCCCTGCCAGCAACCTGGCGGGTAAGGAAGCTAGAGGCTG
GGGAGGCGCCGGAAGAAGCCGCCGCCCAGCTGAGGGCCCTCCAACTAACC
CTCCAGCACCTGGAGGTGGCAGCAGCAGCAGCAAAGCCTTCCAGCTCAAG
TCTCGCCTGCTCAGTCCACTCAGCAGCGCACGCCTGCCTCCTGAACCAGG
ACTGTCTGACAGCTACAGCTTCGACTATCCCTCGGACATGGGACCTAGAC
GGCTCTTCAGCCACCCACGGGAACCAGCCCTTGGGCCTCACGGACCCAGC
CGACACAAGATGTCTCCTCCACCAAGTGGCTTCGGCGAACGGTAG
```

The term "RAVER1" refers to a gene encoding ribonucleoprotein that is the co-repressor of polypyrimidine tract binding protein 1 (PTBP1), perhaps the most well studied splicing repressor. An example is a human RAVER1 having NCBI mRNA Reference Sequence: NM_133452.2 and a NCBI Protein Reference Sequence: NP_597709.2.

The term "RAVER1 splicing repressor domain" refers to a functional part of function part of RAVER1 that includes, as examples, the following protein sequences:

(a) Amino acids 450-643 of the NCBI Protein Reference Sequence:

```
NP_031401.1 (SEQ ID NO: 6):
GKPPPLLPSVLGPAGGDREALGLGPPAAQLTPPPAPVGLRGSGLRGLQKD

SGPLPTPPGVSLLGEPPKDYRIPLNPYLNLHSLLPASNLAGKEARGWGGA

GRSRRPAEGPPTNPPAPGGGSSSSKAFQLKSRLLSPLSSARLPPEPGLSD

SYSFDYPSDMGPRRLFSHPREPALGPHGPSRHKMSPPPSGFGER
```

(b) Amino acids 450-756 of the NCBI Protein Reference Sequence NP_031401.1

```
(SEQ ID NO: 7):
GKPPPLLPSVLGPAGGDREALGLGPPAAQLTPPPAPVGLRGSGLRGLQKD

SGPLPTPPGVSLLGEPPKDYRIPLNPYLNLHSLLPASNLAGKEARGWGGA

GRSRRPAEGPPTNPPAPGGGSSSSKAFQLKSRLLSPLSSARLPPEPGLSD

SYSFDYPSDMGPRRLFSHPREPALGPHGPSRHKMSPPPSGFGERSSGGSG

GGPLSHFYSGSPTSYFTSGLQAGLKQSHLSKAIGSSPLGSGEGLLGLSPG

PNGHSHLLKTPLGGQKRSFAHLLPSPEPSPEGSYVGQHSQGLGGHYADSY

LKRKRIF
```

The term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "TDP-43" is a transactivation response element DNA-binding protein 43 (TDP-43, TARDBP), is a heterogeneous nuclear ribonucleoprotein (hnRNP). An example is a human TDP-43 having NCBI mRNA Reference Sequence: NM_007375.3 and NCBI Protein Reference Sequence: NP_031401.1

The term "ZFP91" is a gene having a cryptic exon (Hg19 assembly) with Human genome coordinates: chr11:58,384,466-58,384,527. The amino acid sequence of translated cryptic exon (SEQ ID NO: 8):

```
QTEEDQISFPSSNISQSFKRNVRSVDLLVDKRHLLIGT
```

BRIEF DESCRIPTION OF THE DRAWINGS

FIG. 1A-1I shows that suppression of cryptic exons can rescue cell death induced by Tdp-43 deletion in humans FIG. 2A-2G shows visualization of TDP-43 associated cryptic exons (*Homo sapiens*). (SEQ ID NOS 14-37, respectively, in order of appearance).

FIG. 3C discloses SEQ ID NOS 38 and 38, respectively, in order of appearance.

DETAILED DESCRIPTION OF THE INVENTION

Figure 3A:
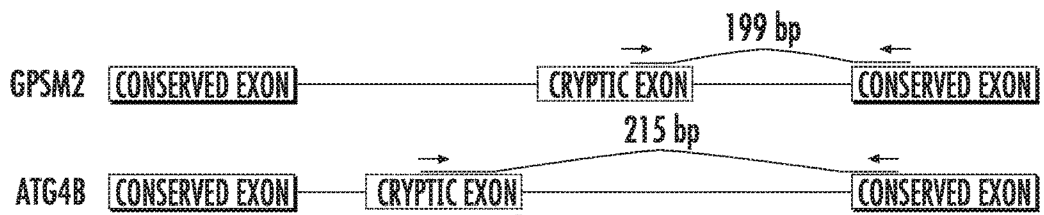
FIG. 3A-3D shows expression of cryptic exons of TDP-43 in human brain autopsies.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide detection and treatment of certain degenerative diseases.

Cytoplasmic aggregation of TDP-43, accompanied by its nuclear clearance, is a key common pathological hallmark of amyotrophic lateral sclerosis and frontotemporal dementia (ALS-FTD). However, a limited understanding of this RNA-binding protein (RBP) impedes the clarification of pathogenic mechanisms underlying TDP-43 proteinopathy. In contrast to RBPs that regulate splicing of conserved exons, the present invention identifies that TDP-43 suppresses the splicing of non-conserved cryptic exons. When TDP-43 is depleted from the cell, these cryptic exons are spliced into mRNAs, often disrupting their translation and promoting nonsense-mediated decay. Moreover, enforced repression of cryptic exons prevents cell death in TDP-43 knockout cells. Importantly, the present invention identifies suppression of cryptic exons is impaired in brains of ALS-FTD, suggesting that this splicing defect underlies TDP-43 proteinopathy. TDP-43 may be the first member of a class of RBPs that serve to maintain the integrity of introns. Thus, the present invention not only has mechanistic and therapeutic implications for ALS-FTD and other human diseases that share TDP-43 pathology, but also reveals more fundamental principles regarding RNA splicing and the evolution of exon-intron structure. TDP-43 is a suppressor of non-conserved cryptic exons; this novel mechanism to maintain intron integrity is compromised in ALS-FTD, indicating that loss of this function underlies TDP-43 proteinopathy.

Failure to properly repress cryptic exons and the concomitant build-up of TDP-43 in cytoplasm with resulting proteinopathy is shown to be a common factor in a number of degenerative diseases. The loss of TDP-43 function can be caused by a mutation in TDP-43 itself or a mutation in one of the many cellular systems (such as autophagy or nuclear import/export) involved in transporting TDP-43 or in removing defective TDP-43. A number of "environmental" factors may also be involved so that a suboptimal functioning TDP-43 system may be pushed over the edge into a non-functioning pathological system. Injury or disease can be sufficient to move the TDP-43 system into a failure mode. The present invention demonstrates that once there is a sufficient loss of TDP-43 function, a cascade is started that results in proteinopathy and cell death. Thus, the incorrect splicing of cryptic exons is both a point for advance detection of disease and for prevention/treatment of disease.

Identification of Tdp-43 Associated Cryptic Exons in Mice

To explore the RNA splicing role of Tdp-43, we took advantage of our previously developed cellular model and assessed the transcriptome of cells lacking Tdp-43 with RNA-seq. These CreER-inducible Tdp-43 knockout mouse embryonic stem (mES) cells (iTDPKO) permitted genetic deletion of Tdp-43 within 2-3 days of 4-hydroxytamoxifen (4HT) treatment and yielded useful gene expression information. However, previous sequencing technologies were unable to provide robust transcriptome-wide splicing data. RNA-seq analyses performed with greater read length and coverage (100 bp paired-end) improved the splicing resolution of the dataset and allowed us to identify cryptic exons in mES cells lacking Tdp-43.

The present invention shows visualization of Tdp-43 associated cryptic exons in iTDPKO cells are depleted of Tdp-43 upon treatment with 4HT. A chromosome ideogram of mouse chromosome 18 depicts the location of Adnp2. In mouse, the most cryptic exons appeared with standard 5' and 3' splice sites (Adipor2, C). Occasionally, cryptic exons could present as transcriptional start sites (Fam122b, C), polyadenylation sites (Synj2 bp, D), or exon extensions (Wbscr22, E). In (F) cryptic exons are flanked by 'UG' tandem repeats. While a large percentage of cryptic exons have repeats immediately downstream of the 5' splice site, 'UG' repeats can also be found immediately upstream of the 3' splice site and directly within the cryptic exon.

These splicing variants have not been previously documented in any public databases and strictly appear in non-conserved regions of the genome. Although some cryptic exons were in-frame and did not contain translation termination (stop) codons, most introduced frameshifts and/or premature stop codons, characteristic of nonsense-mediated decay (NMD). Indeed, several genes that encoded these non-conserved cryptic NMD exons were previously reported by our group to be among the highest down-regulated genes following Tdp-43 depletion—e.g. Fam73a, Usp15, Tecpr1, Ptcd2, and A230046K03Rik. Additionally, most standard cryptic exons appeared to be of normal length (30-300 bp) and did not harbor clear "consensus" exon enhancer elements. Finally, we identified a subset of non-standard cryptic exons that could be categorized as alternative transcriptional start sites, premature polyadenylation sites, or expansions of conserved canonical exons. Interestingly, several cryptic exon extensions were exceptionally long (>1,000 bp).

To determine whether these cryptic exons were direct targets of Tdp-43 binding or missplicing events caused by indirect downstream effects, we looked for evidence of protein-RNA association. It is well established that Tdp-43 has a very high affinity for 'UG' repeats, with a Kd of 14 nM for only 6 repeats. As predicted, long stretches of 'UG' dinucleotide repeats were found adjacent to each cryptic exon, strongly suggesting that Tdp-43 localizes, or binds, to these flanking repeats to act as a general splicing suppressor. Interestingly, the splicing suppressor activity of Tdp-43 appeared to be location independent; 'UG' repeats were observed upstream, downstream, or internal to the cryptic exons. Further evidence of Tdp-43's direct role in suppressing cryptic exons came from previous HITS-CLIP data that mapped all the RNA sequences with which Tdp-43 directly binds and interacts. As expected, clusters of HITS-CLIP reads were mapped onto cryptic exons, suggesting that Tdp-43 mediates its effect on cryptic exons through a direct interaction. Together, these findings strongly support the idea that TDP-43 acts as a splicing suppressor of non-conserved cryptic exons.

The present invention shows that Tdp-43 directly interacts with cryptic exons. Tdp-43's direct binding sites were mapped with HITS-CLIP. Using this HITS-CLIP dataset, we can see that Tdp-43 directly interacts with many cryptic exon sequences. This interaction can be seen for cryptic polyadenylation sites (Synj2 bp) transcriptional start sites (Sptbn4), exon extensions (Wbscr22) and standard cryptic exons (Spata7, A230046K03Rik, Ptcd2).

Suppression of non-conserved cryptic exons and rescue of cell death by a splicing repressor is shown in FIG. 1. In (A) one sees a diagram of the GFP, N-terminus TDP-43, RAVER1 splicing repressor domain chimeric construct (GTR). Predicted molecular weight is 77 kD. FIG. 1 (B) shows the Western blot using an antibody that recognizes mouse/human N-terminus of Tdp-43. While iTDPKO cells are not viable when depleted of Tdp-43, GTR1 cells are fully viable. Note that GTR1 cells lack any endogenous Tdp-43 (43 kD) and instead express the chimeric GTR construct (77 kD). In (C) GTR1 cells can be grown feeder free and develop into well-formed spheres, characteristic of normal ES cells. From left to right: bright field, GFP, overlay. FIG. 1 (D) shows that the doubling rate is unchanged between iTDPKO and GTR1 cells. Suppression of cryptic exons can be seen for various types of cryptic exons; here, standard types (Adipor2, E), polyadenylation sites (Zfp809, F), and exon extensions (Wbscr22, G). However, some cryptic exons are only partially rescued (Synj2 bp, H). FIG. 1 (I) shows RNA-seq transcript expression levels for Tdp-43 knockout cells and GTR1 rescue cells compared to untreated iTDPKO cells (Control). The top 124 downregulated/up-regulated genes in the Tdp-43 knockout cells (fold change less than −3 and greater than +3) were restored to normal levels in the GTR1 rescued cells, with the fold change mostly ranging from −1.5 to 1.5. Full transcript expression data is provided in the Table S4.

We next wanted to establish whether these cryptic exons were a main contributor to the cell death observed when Tdp-43 is depleted from the cell. To this end, we set out to design a construct to generate a fusion protein coupling TDP-43's N-terminal fragment (N-TDP; aa1-267) to a well characterized splicing suppressor domain, in place of TDP-43's C-terminal fragment (C-TDP; aa268-414) (FIG. 1A). N-TDP contains a dimerization domain, nuclear localization signal (NLS), and two 'UG' binding RNA recognition motifs (RRM1, RRM2), but is not believed to be involved in the protein-protein interactions that mediate its cellular function (33). Indeed, N-TDP alone is insufficient to act as a splicing repressor (34, 35). In contrast, C-TDP is a glycine rich, prion-like domain (36) that harbors the vast majority of mutations associated with ALS and is believed to mediate protein-protein interactions important for splicing (3).

To replace C-TDP in our fusion protein, we selected the minimal splicing repressor domain derived from ribonucleoprotein, PTB-binding 1 (RAVER1) (37, 38). RAVER1 is the co-repressor of polypyrimidine tract binding protein 1 (PTBP1), perhaps the most well studied splicing repressor. By coupling a GFP tagged N-TDP to the minimal splicing repressor from RAVER1, we engineered a vector to express a chimeric protein, termed GTR, that retained TDP-43's ability to bind to 'UG' repeats but replaced its complex C-terminal functional domain with a simple splicing repressor (FIG. 1A). Within the cell, GTR is predicted to translocate into the nucleus, bind to 'UG' repeats and inhibit the splicing of cryptic exons.

Figure 4A:
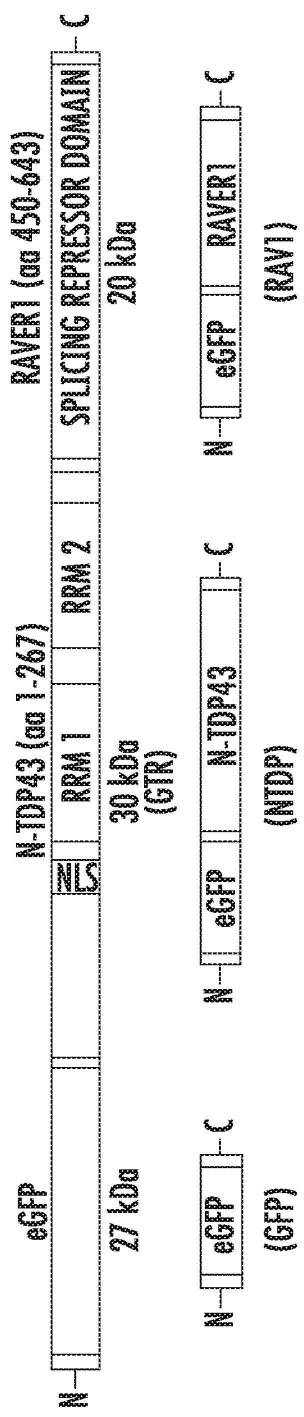
FIG. 4A-4B shows flow cytometry analysis of GTR electroporation showing rescue.
Figure 4B:
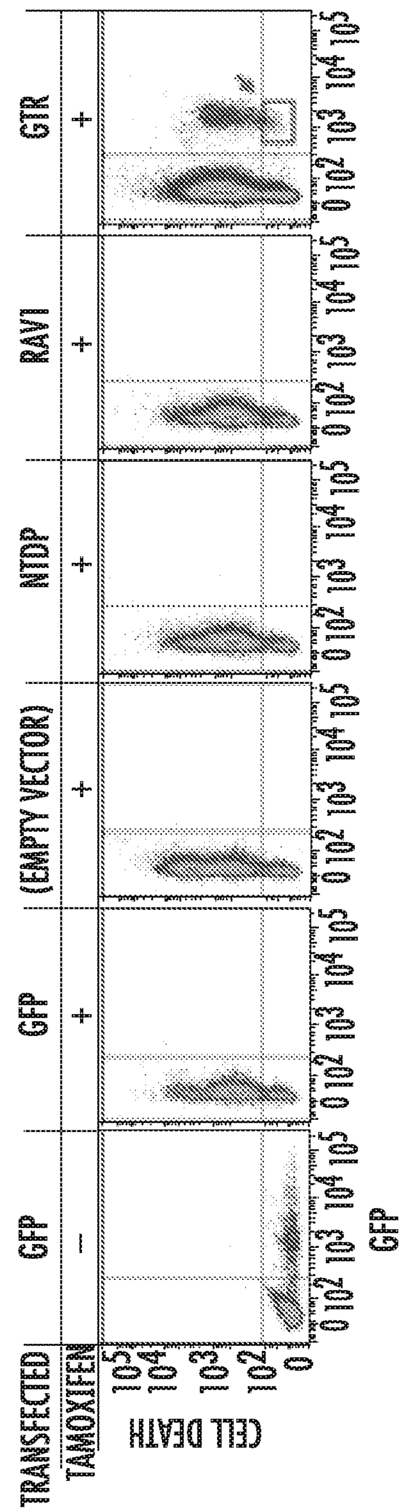

The GTR construct, along with associated controls, was then transiently transfected into 4HT treated iTDPKO cells, which were then screened for survivors by flow cytometry (FIG. 4). After exposure to 4HT, the vast majority of Tdp-43 depleted iTDPKO cells undergo apoptosis, as indicated by a red fluorescent cell viability stain (FIG. 4). While 4HT treated iTDPKO cells transfected with control constructs also failed to survive, a portion of those transfected with the GTR construct remained viable (FIG. 4). These results suggest that the failure of suppression of cryptic exons contributes to lethality in cells lacking Tdp-43.

FIG. 4 shows flow cytometry analysis of GTR electroporation. (A) The GFP, N-terminus TDP-43, RAVER1 splicing repressor domain chimeric construct (GTR) and associated controls were electroporated into iTDPKO cells and analyzed after 4 days of 4HT treatment. (B) Flow cytometry analysis was performed to visualize any surviving cells. Horizontal axis is the GFP channel, indicating successfully transfected cells. The vertical axis represents cell death, which was measured using Sytox red, a membrane-impermeable red fluorescent nucleic acid dye that only labels compromised cells. Transfection positive control (GFP transfected, untreated) demonstrates that cells can be successfully electroporated and sorted by GFP signal. Sytox positive control (GFP transfected, 4HT treatment) underwent dramatic apoptosis and GFP signal was lost due to caspase degradation. All other experimental conditions (negative control empty vector, NTDP and RAV1) also underwent complete apoptosis after 4HT treatment with the exception of GTR. A subset of the GTR transfected cells retained GFP signal, indicating that they had not undergone apoptosis (red box). It will be appreciated that the GTR construct or a similar construct between the N-terminal regions of TDP-43 and some other minimal splicing repressor domain is likely to become an important therapeutic agent for ALS-FTD because they modulate splicing of cryptic exons.

To rule out the possibility that this rescue was only a transient effect of the GTR construct, we generated a stably transfected line of Tdp-43 deficient cells expressing GTR, termed GTR1 (FIG. 1B). Remarkably, the growth rate of GTR1 cells was almost identical to iTDPKO cells (FIG. 1D) and the majority of upregulated and downregulated transcripts in Tdp-43 knockout cells were also restored to normal values in GTR1 cells (FIG. 2I), including several transcripts significantly downregulated due to nonsense-mediated decay (NMD) in Tdp-43 deficient iTDPKO cells (please see Table 1 below). To verify that the rescue effect was correlated with suppression of cryptic exons, we performed RNA-seq analysis of the GTR1 cells. Indeed, while some cryptic exons were only partially suppressed (FIG. 1H), the majority of cryptic exons were highly suppressed (FIG. 1E-G). These findings are consistent with the view that a deficiency in suppressing cryptic exons is a major determinant of cell death associated with depletion of Tdp-43.

Table 1 shows that cryptic exon mediated NMD is alleviated in GTR1 cells. Several transcripts are dramatically reduced due to cryptic exon mediated NMD. These transcripts are restored back to normal levels of expression in GTR1 rescued cells. While most transcripts are downregulated due to NMD, transcripts can also appear downregulated due to premature polyadenylation sites (Gtf2e2) or upregulated due to cryptic exons acting as alternate transcription start sites (Ahnak). In both cases, transcript dysregulation was reversed in GTR1 cells. Complete list of mouse cryptic exons is provided in the supplementary materials.

TABLE 1

| Symbol | Gene Name | Cryptic Exon Length (bp) | Control (FPKM) | K0 (FPKM) | GTR1 (FPKM) | Control vs K0 (FC) | Control vs GTR1 (FC) | NMD | Poly A | Inf. Ins. | Start Site |
|---|---|---|---|---|---|---|---|---|---|---|---|
| Usp15 | Ubiquitin Specific Peptidase15 | 164 | 17.9 | 2.0 | 8.7 | −9.1 | −2.1 | Y | . . . | . . . | . . . |
| Adipor2 | Adiponectin Receptor 2 | 59 | 76.3 | 23.8 | 71.3 | −3.2 | −1.1 | Y | . . . | . . . | . . . |
| A230046K03Rik | WASH Complex Subunit 7 | 198 | 29.1 | 9.1 | 14.5 | −3.2 | −2.0 | Y | . . . | . . . | . . . |
| Nme6 | NME/NM23 Nucleoside Diphosphate Kinase 6 | 148 | 25.7 | 12.0 | 18.5 | −2.1 | −1.4 | Y | . . . | . . . | . . . |
| Mib1 | Mindbomb E3 Ubiquitin Protein Ligase 1 | 59 | 10.3 | 5.5 | 10.7 | −1.9 | 1.0 | Y | . . . | . . . | . . . |
| Gtf2e2 | General Transcription Factor IIE Subunit 2 | 1005 | 45.9 | 29.5 | 40.9 | −1.6 | −1.1 | . . . | Y | . . . | . . . |
| Wbscr22 | Williams Beuren Syn. Chr. Region 22 | 103 | 64.3 | 46.6 | 61.7 | −1.4 | −1.0 | Y | . . . | . . . | . . . |
| Ahnak | AHNAK Nucleoprotein | 365 | 24.0 | 125.7 | 25.7 | 5.2 | 1.1 | . . . | . . . | . . . | Y |

Discovery of Human-Specific Cryptic Exons in TDP-43 Knockdown Cells

FIG. 2 (A) TDP-43 protein levels are greatly reduced when HeLa cells are treated with TDP-43 specific siRNA, compared to treatment with negative control siRNA (asterisk indicates nonspecific band). FIG. 2 (B) Visualization of the cryptic exon located in EPB41L4A. Chromosome ideogram of human chromosome 5 (hg19) shows the genomic location of EPB41L4A (red bar). Zoom in of gene annotation demonstrates that cryptic exons (green arrows) are present in the human genome and reside in non-conserved regions. FIG. 2(C-F) shows the information for IRF9, KRT7, GPSM2, INSR; transcriptional start site, exon extension, standard cryptic exon, polyadenylation site.

Since murine cryptic exons were embedded within non-conserved sequences of the mouse genome, we predicted that human cryptic exons would be located in different regions of the human genome. To determine whether the mechanism of cryptic exon suppression was conserved in humans, we treated HeLa cells with siRNA that specifically targeted TDP-43 and observed a marked reduction in the level of TDP-43 as compared to that of control (FIG. 2A). As predicted, RNA-seq analysis yielded a set of cryptic exons that appeared across the human genome (FIG. 2B-F). Human TDP-43 associated cryptic exons were flanked by ‘UG’ tandem repeats (FIG. 2G) and were classified like those of the mouse: standard cryptic exons (FIG. 2B), transcriptional start sites (FIG. 2C), exon extensions (FIG.

2D) and premature polyadenylation sites (FIG. 2F). Furthermore, no overlap was found when comparing coordinates of cryptic exons between mouse and human.

These observations imply that while the general mechanism of cryptic exon suppression is conserved, the RNA targets of TDP-43 are distinct between species. Consequently, we identified a subset of dysregulated genes that were direct targets of human TDP-43 (Table 2, below). Each of these transcripts incorporates a disruptive cryptic exon when human TDP-43 is depleted from the cell. Remarkably, these identified genes could play a key role in the pathogenesis of ALS-FTD; major pathways that were affected include glycolysis (PFKP, INSR), autophagy (ATG4B), nuclear import/export (RANBP1) and neuromuscular junction formation (AGRN).

Table 2 shows TDP-43 cryptic exon missplicing influences a specific subset of human genes. In humans, TDP-43 cryptic exons target an entirely different subset of transcripts when compared to mouse cryptic exons. Of note, PFKP and INSR are involved in glycolysis, ATG4B is a major player in autophagy, RANBP1 regulates nuclear import and export, and AGRN is essential for the formation of the neuromuscular junction. Taken together, these misspliced transcripts form an intriguing model that could help clarify the pathogenesis of ALS-FTD.

Figure 3B:
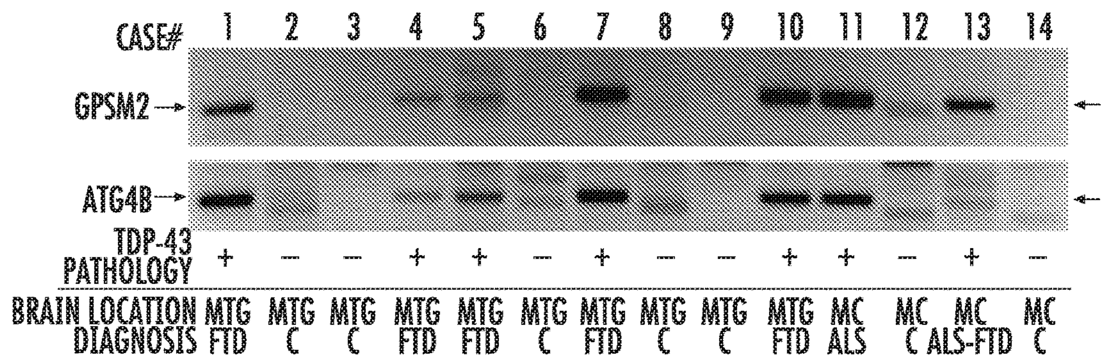
Figure 3C:
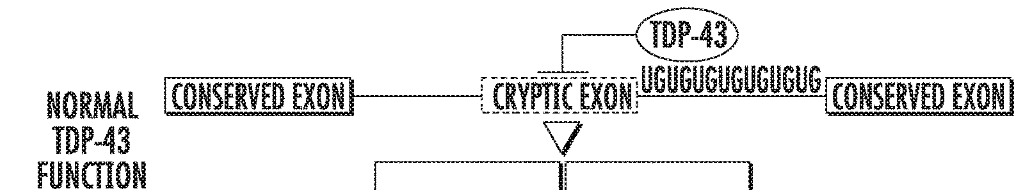
Figure 3D:
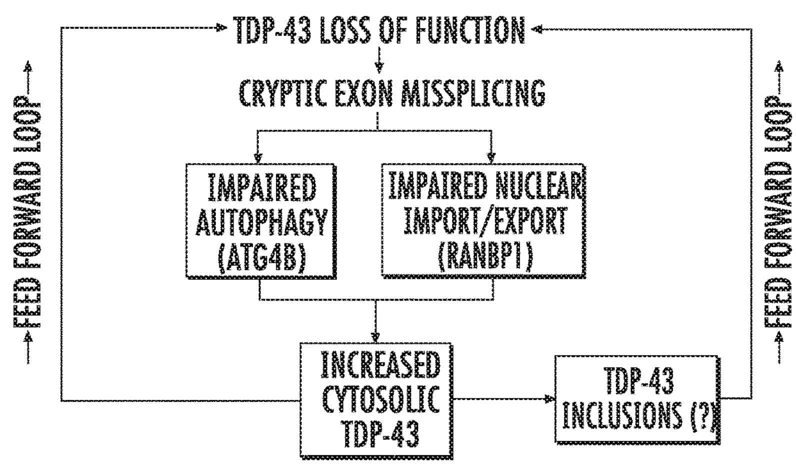

FIG. 3(A) is a diagram of RT-PCR reaction. Primers were designed to amplify only the cryptic exon splice junction. FIG. 3(B) Bands are clearly detected at 199 bp (GPSM2) and at 215 bp (ATG4B) for all cases that display TDP-43 proteinopathy; control cases do not display these bands. Full gel images and case demographics are provided in supplemental data. Note that cases #1, #7, and #13 are positive for C9ORF72 expansions while all other disease cases are sporadic. FIG. 3(C) Mechanistic diagram illustrating TDP-43's function as a suppressor of non-conserved cryptic exons. Normally, TDP-43 binds to 'UG' tandem repeats across the genome, some of which neighbor cryptic exons. At these locations, TDP-43 acts as a splicing repressor to prevent cryptic exon splicing. When TDP-43 function is lost, cryptic exons are no longer suppressed and instead cause disruptions in the mRNA transcripts that are spliced into. FIG. 3(D) Two important mRNAs disrupted by TDP-43 associated cryptic exons (ATG4B, RANBP1) serve to ensure proper turnover of TDP-43 in the cytoplasm. This model suggests a possible mechanism of vulnerability in human disease: TDP-43 loss of function causes cryptic exon missplicing, which further exacerbates TDP-43 loss of function, producing a feed forward loop.

Having identified a set of cryptic exons that TDP-43 regulates in humans, we then screened postmortem brain

TABLE 2

| Symbol | Gene Name | Cryptic Exon Length (bp) | Control (FPKM) | Knockdown (FPKM) | Fold Change | Cryptic vs. Total (%) | NMD | Poly A | Inf. Ins. | Start Site |
|---|---|---|---|---|---|---|---|---|---|---|
| PFKP | Phosphofructokinase, P-type | 263 | 95.5 | 14.9 | −6.4 | 46 | Y | . . . | . . . | . . . |
| PKN1 | Protein Kinase N1 | 230 | 26.2 | 6.5 | −4.1 | 20 | Y | . . . | . . . | . . . |
| RNFT2 | Ring Finger Protein, Tm2 | 689 | 2.9 | 0.9 | −3.1 | 40 | . . . | Y | . . . | . . . |
| KDELC2 | KDEL Motif Protein 2 | 364 | 17.3 | 6.4 | −2.7 | 21 | Y | . . . | . . . | . . . |
| RANBP1 | RAN Binding Protein 1 | 118 | 114.2 | 47.8 | −2.4 | 9 | Y | . . . | . . . | . . . |
| INSR | Insulin Receptor | 198 | 1.9 | 0.8 | −2.3 | 59 | . . . | Y | . . . | . . . |
| CEP72 | Centrosomal Protein 72 kDa | 124 | 16.1 | 8.1 | −2.0 | 85 | Y | . . . | . . . | . . . |
| GPSM2 | G-Protein Signaling Modulator 2 | 115 | 21.6 | 11.0 | −2.0 | 14 | Y | . . . | . . . | . . . |
| ATG4B | Autophagy Related 4B | 204 | 6.8 | 3.8 | −1.8 | 28 | Y | . . . | . . . | . . . |
| EPB41L4A | Band 4.1-Like Protein 4A | 75 | 14.4 | 12.1 | −1.2 | 100 | . . . | . . . | . . . | . . . |
| AGRN | Agrin Proteoglycan | 96 | 26.4 | 44.2 | 1.7 | 32 | . . . | . . . | Y | . . . |
| IRF9 | Interferon Regulatory Factor 9 | 189 | 2.9 | 27.8 | 9.6 | 19 | . . . | . . . | Y | Y |
| TARDBP | TAR DNA Binding Protein 43 | . . . | 37.0 | 9.3 | −4.0 | . . . | . . . | . . . | . . . | . . . |

Detection of TDP-43 Associated Cryptic Exons in Brains of ALS-FTD

The present invention showed sequence and alignment validation of cryptic exon RT-PCR based on full images of 2% agarose DNA gels. Designing primers across cryptic exon sequences is difficult due to repetitive sequences. Likewise, the abundance of transcripts that contain cryptic exons is very low in human brain tissue since the vast majority of cells do not demonstrate TDP-43 proteinopathy. Therefore, high levels of background are inevitable. Nevertheless, relatively clean primers were identified for two genes, ATG4B and GPSM2, and their RT-PCR products can be clearly identified at 215 bp (ATG4B) and 199 bp (GPSM2). Gel purification and sequencing of these RT-PCR bands confirms that these DNA products precisely correspond to the predicted cryptic exon splice junctions. To visualize this, sequencing data was aligned to the human genome using BLAT thick bands in the sequence alignment indicate DNA sequences that are present in the RT-PCR product, thin bands represent sequences that have been spliced out. Sequence alignment demonstrates clear overlap with cryptic exon (green arrow) and completely matches the predicted the splice junctions.

tissues from an ALS-FTD cohort for the presence of these cryptic exons. All ALS-FTD cases that were examined exhibited TDP-43 proteinopathy and were sporadic or C9ORF72 positive. Total RNA was extracted from disease and control brains and subjected to RT-PCR analysis. From our set of human TDP-43 targets (Table 2), we initially selected cryptic exons that did not contain highly repetitive sequences and allowed for the identification of unique primers. PCR products were amplified across the cryptic exon splice junctions of two genes, GPSM2 and ATG4B (FIG. 3A). Importantly, while PCR products of expected sizes were not observed in controls, PCR products corresponding to these cryptic exons were readily observed in all ALS-FTD cases tested (FIG. 3B). We confirmed that these RT-PCR products were indeed amplified across cryptic exon junctions by DNA sequencing analysis. Together, these data establish that the suppression of non-conserved cryptic exons is compromised in the brains of ALS-FTD.

Our discovery that TDP-43 functions as a splicing suppressor of non-conserved cryptic exons has led us to identify a defect in this regulatory mechanism that could underlie TDP-43 proteinopathy in ALS-FTD. These findings offer new insights into the biology of RNA splicing and intron integrity as well as mechanistic and therapeutic implications for human disease. Acting as an hnRNP within the context of other splicing factors, TDP-43 could serve as an alternative splicing regulator for conserved exons. However, this study suggests that TDP-43's primary function lies deep within the distal introns of the genome, where cryptic exons reside. Our finding that TDP-43 binds to 'UG' repeats adjacent to these non-conserved cryptic exons to suppress their splicing now offers a mechanism whereby the integrity of introns can be maintained (see model in FIG. 3C). We propose that under normal conditions, TDP-43 acts as a guardian for the integrity of introns by suppressing non-conserved cryptic exons (FIG. 3C, upper panel). However, under conditions of TDP-43 depletion, these cryptic exons are spliced into mRNAs, often leading to NMD and the downregulation of the associated proteins (FIG. 3C, lower panel). Thus, it is predicted that TDP-43 loss-of-function would impact critical pathways important for cellular function when normal intron splicing is compromised (FIG. 1). In support of this model, we demonstrated that cell death in mouse cells associated with deletion of Tdp-43 can be rescued by restoring the suppression of cryptic exons (FIG. 2). We emphasize that while TDP-43 associated cryptic exons identified in human cells affect an entirely different set of genes when compared with those of mice, the mechanisms regarding the suppression of cryptic exons is conserved. Many of these genes undergo NMD cryptic exons and participate in key cellular pathways, including ATG4B, a gene critical for the initiation of autophagy (40, 41) and RANBP1, a GEF involved in the regulation of nuclear import/export (42, 43). While these targets will be validated in the future, we envision a model where the failure to suppress cryptic exons within genes such as ATG4B and RANBP1 would lead to a feed forward loop that exacerbates TDP-43 proteinopathy in ALS-FTD (refer to model in FIG. 3D) by increasing the cytoplasmic concentration of TDP-43. The cryptic exon-mediated disruption of ATG4B and RANBP1 could converge to increase cytosolic level of TDP-43 and drive TDP-43 aggregation by inhibiting autophagy and reducing nuclear import of TDP-43; such a mechanism would indicate a unique vulnerability for this protein and possibly explain the observation of TDP-43 proteinopathy across a wide range of human disease. Furthermore, other potential pathogenic mechanisms such as impairment of axonal transport of TDP-43 mRNA granules or alteration of dynamics of RNA granule assembly may directly impact cryptic exon missplicing.

Figure 5:
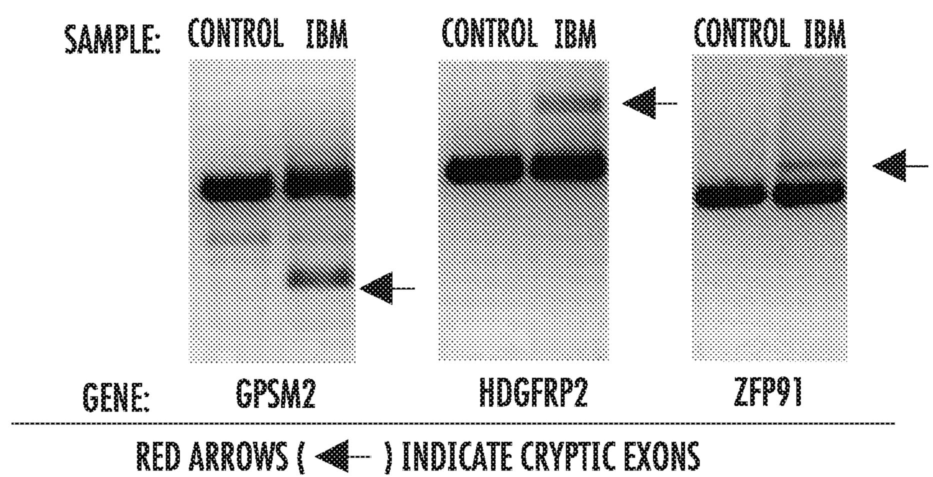
FIG. 5 shows that like ALS-FTD, the muscle disease inclusion body myocytosis (IBM) shows transcription of cryptic exons.

While TDP-43 is capable of binding to 'UG' dinucleotide repeats across the entire genome, its subset of suppressed cryptic exons in both mice and humans is relatively small (<50 genes). An intriguing explanation could be that TDP-43 is the first member of a new class of hnRNPs whose role is to suppress various cryptic exons and maintain intron integrity across the genome. Examples could include RNA-binding proteins implicated in ALS-FTD that do not exhibit TDP-43 proteinopathy, e.g. FUS (46, 47), MATR3 (48), hnRNPA2B1 and hnRNPA1 (45) or others yet to be characterized. Many other simple sequence repeats exist in the genome aside from 'UG' repeats and these repetitive sequences could certainly serve as binding sites for suppressors of cryptic exons. Furthermore, the concept of global cryptic exon suppression is an interesting mechanism for the evolution of exons. Because these cryptic exon sites are not conserved, they are not subject to selective pressure and can thus accumulate mutations. Although speculative at present, it is plausible that mutations within the 'UG' rich domains that TDP-43 uses to suppress cryptic exons could represent genetic susceptibility factors that predispose individuals to ALS-FTD. We envision that current whole genome sequencing efforts may allow us to test such a possibility. More broadly, our findings point to the possibility that loss of TDP-43 function could also occur in other human diseases exhibiting TDP-43 proteinopathy such as Alzheimer's disease, inclusion body myositis (see FIG. 5) and Paget's disease of bone with frontotemporal dementia. The targets and mechanisms identified in this study for ALS-FTD could be readily evaluated for these other human diseases.

Although suppression of cryptic exons was restored in Tdp-43 deleted cells by an unrelated splicing repressor, determining which targets are critical for rescue from cell death remains to be demonstrated. Future studies that establish the functional roles of the human targets of TDP-43 in iPS or other derived cells will have important therapeutic implications. The remarkable rescue of cell death by the GTR fusion protein offers the opportunity to test a potential therapeutic strategy: direct suppression of non-conserved cryptic exons in neurons of ALS-FTD may attenuate neuronal death. We have developed mouse models showing that neurons lacking Tdp-43 in brain or spinal cord exhibit age dependent neurodegeneration as well as defective cryptic exon suppression (data not shown); these models will be instrumental for validating such a therapeutic strategy. For example, AAV9 viral delivery of construct encoding the GTR protein in mice lacking Tdp-43 in neurons will allow one to test, in vivo, whether neuronal loss can be attenuated. If successful, such a therapeutic strategy could be rapidly translated into the clinic. Moreover, the observation that cryptic splicing defects can be observed in brains of ALS-FTD suggests that these TDP-43 targets represent biomarkers for ALS-FTD. We envision the development of specific antibodies as well as nucleic acid probes to detect these novel spliced exons in cerebral-spinal fluid (CSF), blood or skeletal muscle of ALS-FTD cases, serving as either early biomarkers of disease or tools to monitor the efficacy of treatments in clinical trials.

Embodiments of the disclosure concern methods and/or compositions for treating and/or preventing a disease manifesting TDP-43 proteinopathy such as inclusion body myocytosis, or amyotrophic lateral sclerosis (ALS). In certain embodiments, individuals with a disease manifesting TDP-43 are treated with a chimeric protein of the present invention, or a nucleic acid that expresses the chimeric protein, and in specific embodiments an individual with ALS is provided a chimeric protein of the present invention.

In certain embodiments, the level to which a chimeric protein of the present invention may inhibit cryptic exon expression may be any level so long as it provides amelioration of at least one symptom of the disease manifesting TDP-43 proteinopathy, including ALS. The level of expression may increase by at least 2, 3, 4, 5, 10, 25, 50, 100, 1000, or more fold expression compared to the level of expression in a standard, in at least some cases. An individual may monitor expression levels of cryptic exon expression using standard methods in the art, such as northern assays or quantitative PCR, for example.

An individual known to have disease manifesting TDP-43 proteinopathy such as ALS, suspected of having such a disease, or at risk for having such a disease may be provided an effective amount of a chimeric protein of the present invention, including an N-terminal domain derived from an N-terminal nucleotide binding domain of TDP-43; and a C-terminal domain derived from a splicing repressor.

Those at risk for a disease manifesting TDP-43 may be those individuals having one or more genetic factors, may be of advancing age, and/or may have a family history, for example.

In particular embodiments of the disclosure, an individual is given a chimeric protein of the present invention, or nucleic acid that expresses the chimeric protein, for a disease manifesting TDP-43 proteinopathy therapy in addition to the one or more other agents that suppress cryptic exon expression. When combination therapy is employed with one or more chimeric proteins, or nucleic acids expressing the chimeric protein, the additional therapy may be given prior to, at the same time as, and/or subsequent to the one or more chimeric proteins, or nucleic acids expression the chimeric proteins.

Certain methods of the disclosure provide for methods of diagnosing a disease manifesting TDP-43 proteinopathy prior to the therapeutic methods of the disclosure, and such diagnosis may occur by any methods or means, including at least genetic marker assay, single-photon emission computed tomography, olfactory system testing, autonomic system testing, or a combination thereof.

Pharmaceutical Preparations

Pharmaceutical compositions of the present invention comprise an effective amount of one or more inhibitors of cryptic exon expression such as a chimeric protein of the present invention, or a nucleic acid that expresses the chimeric protein of the present invention such as a virus, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one inhibitor of cryptic exon expression or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inhibitor of cryptic exon expression, such as the chimeric protein, may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The inhibitor of cryptic exon expression (such as a chimeric protein of the present invention) may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in a composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include inhibitors of cryptic exon expression (such as a chimeric protein or a nucleic acid that expresses a chimeric protein) one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, a inhibitor of cryptic exon expression may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the inhibitor of cryptic exon expression are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, inhibitors or cryptic exon expression may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 67,537,514, 6,613,308, 5,466,468, 5,543, 158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound inhibitor of cryptic exon expression (i.e. a chimeric protein of the present invention) may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles.

Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an inhibitor of cryptic exon expression (for example, a chimeric protein of the present invention or nucleic acid that expresses a chimeric protein of the present invention such as a virus) may be comprised in a kit.

The kits may comprise a suitably aliquoted the inhibitor of cryptic exon expression and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the inhibitor of cryptic exon expression and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The inhibitors of cryptic exon expression composition(s) may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES/METHODS

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Cell Culture and Manipulation

Mouse ES cells were cultured on 0.1% Gelatin with feeder free media using the 2-inhibitor, or 2i method. Briefly, a 1:1 mixture of DMEM/F12 (Life Tech., 11320033) and Neurobasal (Life Tech., 21103049) was supplemented with N-2 (Life Tech., 17502048), B-27 w/RA (Life Tech., 17504044), Insulin (Life Tech., 12585014), GlutaMAX (Life Tech., 35050061) and BSA (Sigma-Aldrich, A8412) to form the base media. GSK36 inhibitor CHIR99021 (CalBioChem, 361571), MEK inhibitor PD0325901 (Sigma-Aldrich, PZ0162), Leukemia Inhibitory Factor (Sigma-Aldrich, L5158) and β-mercaptoethanol (Sigma-Aldrich, M3148) were added to the base media to form the completed serum free ES cell culture media. To induce Cre recombination and deletion of the floxxed Tardbp allele, ES cells were treated with 100 ng/mL of (Z)-4-Hydroxytamoxifen (Sigma-Aldrich, H7904) for 2-4 days. Transfection of ES cells was performed using the MicroPulser Electroporator (Biorad) with an exponential decay curve using a voltage of 0.32 kV and capacitance of 250 uF.

HeLa cells were cultured in Dulbecco's Modified Eagle's Medium (Corning, 10-017-CV) supplemented with 1× GlutaMAX (Life Tech., 35050061), 10% FBS (Corning, 35-010-CV). Knockdown of TDP-43 was performed by transfecting siRNA targeting the TARDBP transcript (Sigma-Aldrich, EHU109221) while control was transfected with negative control siRNA (Life Tech., 4390843). Transfection of siRNA was achieved using Lipofectamine 3000 (Life Tech., L3000008).

RNA Preparation and RNA-Seq Analysis

RNA was extracted from cell culture samples using TRIzol (Life Tech., 15596-026) and RNeasy Mini Kits (Qiagen, 74104). RNA from human brain tissue was extracted in a similar fashion but required an additional homogenization step (trituration using 1 mL syringe w/20-gauge needle) after placing tissue in TRIzol. Total RNA was then processed using the TruSeq Stranded Total RNA Library Prep Kit (Illumine) to construct 100-bp paired end stranded RNA-seq libraries. Sample libraries were then sequenced on a HiSeq 2500 to generate approximately 50 million reads per sample. Samples were then de-multiplexed and converted into fastq files.

Fastq files were aligned to mouse and human genomes using TopHat and annotated using Cufflinks (53) on Galaxy (54), an open-source, web-based bioinformatics platform. Cryptic exons were initially identified through manual screening of novel exons annotated by Cufflinks that were highly abundant in the Tdp-43 knockout dataset but not control. TopHat aligned data was then displayed to the UCSC Genome Browser (55) to visualize RNA-seq coverage.

Gene ontology analysis of enriched terms were determined using the DAVID Bioinformatics Resource 6.7: Functional Annotation Tool (56).

GTR1 Vector Construction and Flow Cytometry

A DNA fragment corresponding to the chimeric junction between aa1-267 of TDP-43 and aa450-643 of RAVER1 was commercially synthesized (Life Tech., GeneArt). Heavily repetitive GC rich regions were mutated to reduce sequence complexity while maintaining amino acid sequence. This N-TDP43, RAVER1 fragment was then genetically cloned into a construct expressing GFP under the EF1α promoter (Addgene, #11154) such that GFP, N-TDP43 and RAVER1 were all inframe. Associated controls (FIG. 4) were designed by restriction digest removal of specific regions from the GTR protein sequence.

Flow cytometry was performed using a FACSCalibur (BD Biosciences). The 488 nm laser was used to measure GFP signal from successfully electroporated cells while the 633 nm laser was used to measure fluorescence from SYTOX Red (Life Tech., S34859), a nucleic acid binding cell viability stain.

RT-PCR of Human Targets cDNA was derived from human brain tissue total RNA (1 ug total RNA/20 ul first strand cDNA reaction) using ProtoScript II (NEB, E6560S). Numerous primers were designed against cryptic exon targets and then screened to identify primer pairs that minimized background bands. Primers that amplify cryptic exon junctions in ATG4B (215 bp) and GPSM2 (199 bp) are listed below:

```
                              (SEQ ID NO: 9)
ATG4B-F: TGTGTCTGGATGTGAGCGTG

                             (SEQ ID NO: 10)
ATG4B-R: TCTAGGGACAGGTTCAGGACG

                             (SEQ ID NO: 11)
GPSM2-F: AGTGGACATGTGGTGGTAAGAA

                             (SEQ ID NO: 12)
GPSM2-R: GCTTCAAAGAATGACACGCCA
```

Both PCR reactions were performed using Phusion High-Fidelity DNA Polymerase (NEB, M0530S) with the following protocol:

(GC Buffer, no DMSO)

Initial Denaturation: 98° C. for 30 s

Initial Denaturation: 98° C. for 30 s

40 Cycles: 98° C. for 8 s

63° C. for 12 s

72° C. for 30 s

Final Extension: 72° C. for 7 min

Hold: 4° C.

PCR products were then gel excised and DNA extracted using the QIAquick Gel Extraction Kit (Qiagen, 28704). Sanger sequencing was performed with the 3730xl DNA Analyzer (Applied Biosystems) and then aligned using Blat to ensure that the amplified product originated from cryptic exon splicing.

Antibodies

The following antibodies were used in this study: mouse/human rabbit polyclonal against N-terminus of TDP-43 (1:5000; Proteintech, 10782-2-AP), human specific mouse monoclonal against TDP-43 (1:5000; Sigma-Aldrich, WH0023435M1); mouse/human monoclonal against GAPDH (1:10,000; Sigma-Aldrich, G8795).

Accession Codes

All sequenced reads reported in this paper have been deposited at the NCBI Sequence Read Archive (SRA) under accession number PRJNA214189.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A chimeric protein comprising the amino acid sequence encoded by SEQ ID NO:13.

* * * * *